US008252817B2

(12) United States Patent
Flamme et al.

(10) Patent No.: US 8,252,817 B2
(45) Date of Patent: Aug. 28, 2012

(54) DIPYRIDYL-DIHYDROPYRAZOLONES AND THEIR USE

(75) Inventors: Ingo Flamme, Reichshof (DE); Jens-Kerim Ergüden, Wülfrath (DE); Felix Oehme, Wuppertal (DE); Kai Thede, Wuppertal (DE); Gunter Karig, Hofheim am Taunus (DE); Alexander Kuhl, Hagen (DE); Hanno Wild, Wuppertal (DE); Joachim Schuhmacher, Wuppertal (DE); Peter Kolkhof, Wuppertal (DE); Lars Bärfacker, Oberhausen (DE); Joachim Hütter, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 669 days.

(21) Appl. No.: 11/919,478

(22) PCT Filed: Apr. 15, 2006

(86) PCT No.: PCT/EP2006/003488
§ 371 (c)(1),
(2), (4) Date: Oct. 30, 2009

(87) PCT Pub. No.: WO2006/114213
PCT Pub. Date: Nov. 2, 2006

(65) Prior Publication Data
US 2010/0035906 A1    Feb. 11, 2010

(30) Foreign Application Priority Data

Apr. 28, 2005    (DE) .......................... 10 2005 019 712

(51) Int. Cl.
*A61K 31/4439*    (2006.01)
*C07D 401/14*    (2006.01)
(52) U.S. Cl. ........................................ 514/333; 546/256
(58) Field of Classification Search .................. 546/256; 514/333
See application file for complete search history.

(56) References Cited

U.S. PATENT DOCUMENTS

| 4,075,003 A | 2/1978 | Beck et al. |
| 4,118,574 A | 10/1978 | Beck et al. |
| 4,663,327 A | 5/1987 | Sasse et al. |
| 4,698,344 A | 10/1987 | Sasse et al. |
| 4,806,540 A | 2/1989 | Sasse et al. |
| 2003/0083351 A1 | 5/2003 | Almstead et al. |
| 2006/0067927 A1 | 3/2006 | Chandrasekaran et al. |
| 2006/0160826 A1 | 7/2006 | Ghanbari et al. |

FOREIGN PATENT DOCUMENTS

| AU | 3808595 A | 5/1996 |
| CA | 1067907 | 6/1977 |
| CA | 2364908 A1 | 9/2000 |
| CA | 2608099 A1 | 11/2006 |
| CA | 2667392 | 2/2008 |
| DE | 2651008 A1 | 6/1977 |
| EP | 165448 A2 | 12/1985 |
| EP | 0183159 | 6/1986 |
| EP | 212281 A1 | 3/1987 |
| WO | WO-96/12706 A1 | 5/1996 |
| WO | WO-00/51989 A1 | 9/2000 |
| WO | 02092573 | 11/2002 |
| WO | 03/051833 A2 | 6/2003 |
| WO | WO-03/074550 A2 | 9/2003 |
| WO | 2004052284 | 6/2004 |
| WO | 2004/089303 A2 | 10/2004 |
| WO | 2004087066 | 10/2004 |
| WO | 2005030121 | 4/2005 |
| WO | 2006/0101903 | 9/2006 |
| WO | 2007/008541 A2 | 1/2007 |

OTHER PUBLICATIONS

Vippagunta et al., "Crystalline Solid", Advanced Drug Delivery Reviews 48 (2001) 3-26.*
Guillory (in Brittain ed.), "Polymorphism, etc.," NY: Marcel Dekker, Inc., 1999, 1-2, 125-181, 183-226.*
Yu et al., "Physical characterization of, etc.," PSTT, vl. 1(3), 118-127 (1998).*
G. Eder: "Allgemeine Pathologie und Pathologische Anatomie," Aufl, Springer Verlag, Berlin, vol. 33, 1990.
R. F. Schmidt et al.: "Physiologie des Menschen," Aufl, Springer Verlag, Berlin, vol. 27, 1997.
G. Löffler et al: "Biochemie und Pathobiochemie," Aufl, Springer Verlag, Berlin, vol. 7, 2003, pp. 1-22.
M. Simons et al.: "Therapeutic Angiogenesis in Cardiovascular Disease," Nat. Rev. Drug. Discov., vol. 2, No. 11, 2003, pp. 863-871.
K-U. Eckardt: "The Potential of Erythropoietin and Related Strategies to Stimulate Erythropoiesis," Current Opinion in Investigational Drugs, vol. 2, No. 8, 2001, pp. 1081-1085.
J. S. Berns: "Should the Target Hemoglobin for Patients with Chronic Kidney Disease Treated with Erythropoietic Replacement Therapy be Changed?" Seminars in Dialysis, vol. 18, No. 1, Jan.-Feb. 2005, pp. 22-29.
K. Caiola et al.: "Use of Erythropoietin in Heart Failure Management," The Annals of Pharmacotherapy, vol. 38, Dec. 2004, pp. 2145-2149.
S. D. Katz: "Mechanisms and Treatment of Anemia in Chronic Heart Failure," Cong. Heart Failure, vol. 10, 2004, pp. 243-247.
G. L. Semenza: "Hypoxia-Inducible Factor 1: Oxygen Homeostasis and Disease Pathophysiology," Trends in Molecular Medicine, vol. 7, No. 8, Aug. 2001, pp. 345-350.
R. H. Wenger et al.: "Oxygen(es) and the Hypoxia-Inducible Factor-1," Biol. Chem., vol. 378, Jul. 1997, pp. 609-616.

(Continued)

*Primary Examiner* — Patricia Morris
(74) *Attorney, Agent, or Firm* — Karen B. King

(57) ABSTRACT

The present application relates to novel dipyridyl-dihydropyrazolones, processes for their preparation, their use for treatment and/or prophylaxis of diseases and their use for the preparation of medicaments for treatment and/or prophylaxis of diseases, in particular cardiovascular and hematological diseases and kidney diseases, and for promoting wound healing.

10 Claims, No Drawings

OTHER PUBLICATIONS

A. C. R. Epstein et al.: "C. elegans EGL-9 and Mammalian Homologs Define a Family of Dioxygenases that Regulate HIF by Prolyl Hydroxylation," Cell, vol. 107, Oct. 5, 2001, pp. 43-54.

R. K. Bruick et al.: "A Conserved Family of Prolyl-4-Hydroxylases that Modify HIF," Science 294, Nov. 9, 2001, pp. 1337-1340.

M. Ivan et al.: "Biochemical Purification and Pharmacological Inhibition of a Mammalian Prolyl Hydroxylase Acting on Hypoxia-Inducible Factor," Proc. Natl. Acad. Sci., vol. 99, No. 21, Oct. 15, 2002, pp. 13459-13464.

L. Aravind et al.: "The DNA-Repair Protein AlkB, EGL-9, and Leprecan Define New Families of 2-Oxoglutarate- and Iron-Dependent Dixygenases," Genome Biology, vol. 2, No. 3, Feb. 19, 2001, pp. 1-8.

C. J. Schofield et al.: "Oxygen Sensing by HIF Hydroxylases," Nature Reviews Molecular Cell Biology, vol. 5, May 2004, pp. 343-354.

J. Büchi et al.: "Synthese und Pharmakologische Eigenschaften Einiger Pyridyl-Pyrazol-5-one," Helv. Chim. Acta, vol. 49, No. 1, 1966, pp. 272-280.

H. Barth et al.: "Konstitution und Synthese des Muscaflavins," Liebigs Ann. Chem., 1981, pp. 2164-2179.

R. A. Evans et al.—Tribluoromethyl-substituted Dedhydrodizepines and Cyanopyrroles form Azido-/Tetrazolo-pyridines, J. Chem. Commun., vol. 15, 1992, pp. 1062-1064.

F. Oehme et al.: "A Nonradioactive 96-well Plate Assay for the Detection of Hypoxia-Inducible Factor Prolyl Hydroxylase Activity," Analytical Biochemistry, vol. 330, 2004, pp. 74-80.

F. Oehme et al.: "Overexpression of PH-4, a Novel Putative Proline 4-Hydroxylase, Modulates Activity of Hypoxia-Inducible Transcription Factors," Biochemical and Biophysical Research Communications, vol. 296, 2002, pp. 343-349.

C. A. Heid et al.: "Real Time Quantitavie PCR," Genome Research, vol. 6, No. 10, 1996, pp. 986-994.

N. Yokoyama et al.: "Synthesis and Structure-Activity Relationships of Oxamic Acid and Acetic Acid Derivatives Related to L-Thyronine," J. Med. Chem., vol. 38, 1995, pp. 695-707.

N. Sperber et al.: "Parasympathetic Blocking Agents. III. N-Alkylpiperidinecarboxylic Esters," J. Am. Chem. Soc., vol. 81, 1959, pp. 704-709.

M. A. A. Meziane et al.: "A New Route to 1-Oxo-1,2-Dihydropyrimido[1,6a]Benzimidazole-4-Carboxylates from Ethyl 2-(Benzimidazol-2-yl)-3-(Dimethylamino)Acrylate Using Solvent-Free Conditions," Synthesis, Jul. 1998, pp. 967-969.

S.P. Singh et al.: "Reaction of 1-[5-Hydroxy-3-Methyl-1-(2-Thiazolyl)-4-Pyrazolyl]-1,3-Butanediones with Phenyl and Heterocyclic Hydrazines: a Convienient Syntheses of 4,5-Bipyrazoles," Indian Journal of Heterocyclic Chemistry, Jul.-Sep. 1993, 3: 5-8.

J. Elguero et al.: "A 1H and 13C NMR Study of the Structure and Tautomerism of 4-Pyrazolylprazolinones," J. Heterocyclic Chem., May-Jun. 1990, 27: 865-870.

West, "Solid Solutions," 1988, Chapter 10, pp. 358 and 365.

Ulrich, "Crystallization: 4. Crystal Characteristics," Kirk-Othmer Encyclopedia of Chemical Technology, Aug. 2002.

B. Djerrari et al.: "3-Methyl-1-(Pyridin-2-yl)-4-(1-Pyridin-2-yl-3-Methyl-1H-Pyrazol-5-yl)-2H-3-Pyrazolin-5(1HI)-one," Acta Crystallographica Section E, Structure Reports Online, 2001, E57, No. 11, pp. o1126-o1127.

Hill et al. "Inhibition of TRPM2 channels by the antifungal agents clotrimazole and econazole," Naunyn Schmiedebergs Arch. Pharmacol, 2004, 370: 277-238, abstract only.

U.S. Appl. No. 12/427,749, filed Apr. 22, 2009, now US Patent No. 8,067,407.

U.S. Appl. No. 12/447,192, filed in US Oct. 12, 2007.

U.S. Appl. No. 12/447,201, filed in US Oct. 26, 2007.

U.S. Appl. No. 12/447,207, filed in US Dec. 21, 2009.

* cited by examiner

DIPYRIDYL-DIHYDROPYRAZOLONES AND THEIR USE

The present application relates to novel dipyridyl-dihydropyrazolones, processes for their preparation, their use for treatment and/or prophylaxis of diseases and their use for the preparation of medicaments for treatment and/or prophylaxis of diseases, in particular cardiovascular and hematological diseases and kidney diseases, and for promoting wound healing.

A deficient supply of oxygen to the human organism or its components which either impairs regular functioning of the organism or its components due to its duration and/or its extent or causes its functioning to break down completely is called hypoxia. Hypoxia can be caused by a reduction in the available oxygen in the air breathed in (e.g. during periods at a great height), by disorders in external respiration (e.g. as a result of disturbed functioning of the lungs or obstruction of the respiratory tract), by a reduction in the cardiac output (e.g. in the event of cardiac insufficiency, acute right ventricular overloading with pulmonary embolism), by too low an oxygen transport capacity of the blood (e.g. as a result of an anemia or intoxication, e.g. with carbon monoxide), locally demarcated by a reduced blood flow as a result of vascular occlusions (ischaemia states typically e.g. of the heart, the lower extremities or the brain, diabetic macro- and microangiopathy) or also by an increased oxygen requirement of the tissue (e.g. as a result of increased muscular work or local inflammations [Eder, Gedigk (ed.), *Allgemeine Pathologie und pathologische Anatomie,* 33rd ed., Springer Verlag, Berlin, 1990]

The human organism is capable to a limited extent of adapting acutely and chronically to situations of reduced oxygen supply. In addition to an immediate response, which includes inter alia an increase in the cardiac output and respiratory output and a local dilation of blood vessels by vegetative-nervous control mechanisms, hypoxia brings about a change in the transcription of numerous genes. The function of the gene products here serves to compensate the oxygen deficiency. Thus, expression of several enzymes of glycolysis and glucose transporter I is enhanced, as a result of which anaerobic ATP production increases and survival of the oxygen deficiency is rendered possible [Schmidt, Thews (ed.), *Physiologie des Menschen,* 27th ed., Springer Verlag, Berlin, 1997; Löffler, Petrides (ed.), *Biochemie und Pathobiochemie,* 7th ed., Springer Verlag, Berlin, 2003].

Hypoxia furthermore leads to enhanced expression of vascular endothelial cell growth factor, VEGF, as a result of which regeneration of blood vessels (angiogenesis) is stimulated in hypoxic tissues. The blood flow through ischaemic tissue is thereby improved in the long term. This counter-regulation is evidently only very inadequate in the case of various cardiovascular diseases and vascular occlusion diseases [overview in: Simons and Ware, *Therapeutic angiogenesis in cardiovascular disease,* Nat. Rev. Drug. Discov. 2 (11), 863-71 (2003)].

Furthermore, in cases of systemic hypoxia expression of the peptide hormone erythropoietin formed predominantly in the interstitial fibroblasts of the kidneys is enhanced. The formation of red blood cells in the bone marrow is thereby stimulated, and the oxygen transport capacity of the blood is therefore increased. This effect has been and is used by high-performance athletes in so-called high altitude training. A decrease in the oxygen transport capacity of the blood e.g. as a result of anemia after hemorrhaging usually causes an increase in erythropoietin production in the kidney. With certain forms of anemia, this regulatory mechanism may be disturbed or its normal value may be set lower. Thus e.g. in patients suffering from renal insufficiency, erythropoietin is indeed produced in the kidney parenchyma, but in significantly reduced amounts with respect to the oxygen transport capacity of the blood, which results in so-called renal anemia. Renal anemia in particular, but also anemias caused by tumors and HIV infection are conventionally treated by parenteral administration of recombinant human erythropoietin (rhEPO). No alternative therapy with an orally available medicament currently exists for this expensive therapy [overview in: Eckardt, *The potential of erythropoietin and related strategies to stimulate erythropoiesis,* Curr. Opin. Investig. Drugs 2(8), 1081-5 (2001); Berns, *Should the target hemoglobin for patients with chronic kidney disease treated with erythropoietic replacement therapy be changed?,* Semin. Dial. 18 (1), 22-9 (2005)]. Recent studies demonstrate that, in addition to its erythropoiesis-increasing action, erythropoietin also has a protective (anti-apoptotic) action on hypoxic tissue, in particular the heart and the brain, which is independent thereof. Furthermore, according to recent studies therapy with erythropoietin reduces the average severity of morbidity in patients with cardiac insufficiency [overviews in: Caiola and Cheng, *Use of erythropoietin in heart failure management,* Ann. Pharmacother. 38 (12), 2145-9 (2004); Katz, *Mechanisms and treatment of anemia in chronic heart failure,* Congest. Heart. Fail. 10 (5), 243-7 (2004)].

The genes described above which are induced by hypoxia have the common feature that the increase in their expression under hypoxia is caused by so-called hypoxia-inducible transcription factor (HIF). HIF is a heterodimeric transcription factor which comprises an alpha and a beta subunit. Three HIF alpha isoforms are described, of which HIF-1 alpha and HIF-2 alpha are highly homologous and are of importance for hypoxia-induced gene expression. While the beta subunit (of which 2 isoforms have been described), which is also called ARNT (aryl hydrocarbon receptor nuclear translocator), is expressed constitutively, expression of the alpha subunit depends on the oxygen content in the cell. Under normoxia, the HIF alpha protein is poly-ubiquitinized and then degraded proteasomally. Under hypoxia this degradation is inhibited, so that HIF alpha dimerizes with ARNT and can activate its target genes. The HIF dimer bonds here to so-called hypoxia-responsible elements (HRE) in the regulatory sequences of its target genes. The HRE are defined by a consensus sequence. Functional HRE have been detected in the regulatory elements of numerous hypoxia-induced genes (overviews in: Semenza, *Hypoxia-inducible factor* 1: *oxygen homeostasis and disease pathophysiology,* Trends Mol. Med. 7 (8), 345-50 (2001); Wenger and Gassmann, *Oxygen(es) and the hypoxia-inducible factor*-1, Biol. Chem. 378 (7), 609-16 (1997)].

The molecular mechanism on which this regulation of HIF alpha is based has been clarified by the works of several independent groups of researchers. The mechanism is conserved from species to species: HIF alpha is hydroxylated by a subclass of oxygen-dependent prolyl 4-hydroxylases, called PHD or EGLN, on two specific prolyl radicals (P402 and P564 of the human HIF-1 alpha subunit). The HIF prolyl 4-hydroxylases are iron-dependent, 2-oxoglutarate-converting dioxygenases [Epstein et al., *C. elegans EGL-9 and mammalian homologs define a family of dioxygenases that regulate HIF by prolyl hydroxylation,* Cell 107 (1), 43-54 (2001); Bruick and McKnight, *A conserved family of prolyl-4-hydroxylases that modify HIF,* Science 294 (5545), 1337-40 (2001); Ivan et al., *Biochemical purification and pharmacological inhibition of a mammalian prolyl hydroxylase acting on hypoxia-inducible factor,* Proc. Natl. Acad. Sci. U.S.A. 99 (21), 13459-64 (2002)]. The enzymes were annotated as prolyl hydroxylases for the first time in 2001 [Aravind and Koonin, *The DNA-repair protein AlkB, EGL-9, and leprecan define new families of 2-oxoglutarate- and iron-dependent dioxygenases*, Genome Biol. 2 (3), research0007.1-0007.8, Epub 2001 February 19].

The pVHL tumor suppressor protein, which together with elongin B and C forms the so-called VBC complex, which adapts the HIF alpha subunit to an E3 ubiquitin ligase, bonds to the prolyl-hydroxylated HIF alpha subunit. Since the prolyl 4-hydroxylation of the HIF alpha subunit and its subsequent degradation takes place as a function of the intracellular concentration of oxygen, HIF prolyl 4-hydroxylases have also been called a cellular oxygen sensor. Three isoforms of these enzymes have been identified: EGLN1/PHD2, EGLN2/PHD1 and EGLN3/PHD3. Two of these enzymes (EGLN2/PHD1 and EGLN3/PHD3) are induced transcriptionally even under hypoxia and are possibly responsible for the lowering of the HIF alpha levels to be observed under chronic hypoxia [overview in: Schofield and Ratcliffe, *Oxygen sensing by HIF hydroxylases*, Nat. Rev. Mol. Cell. Biol. 5 (5), 343-54 (2004)].

Selective pharmacological inhibition of HIF prolyl 4-hydroxylases brings about the increase in the gene expression of HIF-dependent target genes and is therefore beneficial for the therapy of numerous disease syndromes. In the case of diseases of the cardiovascular system in particular, an improvement in the course of the diseases is to be expected from induction of new blood vessels and the change in the metabolic situation of ischaemic organs from aerobic to anaerobic ATP production. An improvement in the vascularization of chronic wounds promotes the healing process, especially in the case of poorly healing ulcera cruris and other chronic skin wounds. The induction of endogenous erythropoietin in certain disease forms, in particular in patients with renal anemia, is likewise a therapeutic goal to be aimed for.

The HIF prolyl 4-hydroxylase inhibitors described hitherto in the scientific literature do not meet the requirements to be imposed on a medicament. These are either competitive oxoglutarate analogues (such as e.g. N-oxalylglycine), which are characterized by their very low action potency, and therefore in in vivo models have as yet shown no action in the sense of an induction of HIF target genes. Or they are iron-complexing agents (chelators), such as desferroxamine, which act as non-specific inhibitors of iron-containing dioxygenases and, although they bring about an induction of the target genes, such as e.g. erythropoietin, in vivo, evidently counteract erythropoiesis by complexing of the available iron.

The object of the present invention is to provide novel compounds which can be employed for treatment of diseases, in particular cardiovascular and hematological diseases.

In the context of the present invention, compounds are now described which act as specific inhibitors of HIF prolyl 4-hydroxylases and on the basis of this specific action mechanism bring about in vivo, after parenteral or oral administration, the induction of HIF target genes, such as e.g. erythropoietin, and the biological processes thereby caused, such as e.g. erythropoiesis.

2-Heteroaryl-4-aryl-1,2-dihydropyrazolones having a bactericidal and/or fungicidal action are disclosed in EP 165 448 and EP 212 281. The use of 2-heteroaryl-4-aryl-1,2-dihydropyrazolones as lipoxygenase inhibitors for treatment of respiratory tract, cardiovascular and inflammatory diseases is claimed in EP 183 159. 2,4-Diphenyl-1,2-dihydropyrazolones having a herbicidal activity are described in DE 2 651 008. The preparation and pharmacological properties of certain 2-pyridyl-1,2-dihydropyrazolones are reported in *Helv. Chim. Acta* 49 (1), 272-280 (1966). WO 96/12706, WO 00/51989 and WO 03/074550 claim compounds having a dihydropyrazolone partial structure for treatment of various diseases.

The present invention provides compounds of the general formula (I)

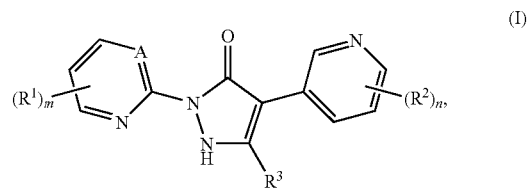

in which

A represents CH or N, $R^1$ represents a substituent chosen from the series consisting of $(C_1-C_6)$-alkyl, trifluoromethyl, halogen, cyano, nitro, hydroxyl, $(C_1-C_6)$-alkoxy, amino, $(C_1-C_6)$-alkoxycarbonyl, hydroxycarbonyl and —C(=O)—NH—$R^4$, wherein $(C_1-C_6)$-alkyl in its turn can be substituted by hydroxyl, $(C_1-C_4)$-alkoxy, amino, mono-$(C_1-C_4)$-alkylamino, di-$(C_1-C_4)$-alkylamino or a group of the formula —NH—C(=O)—$R^5$, —NH—C(=O)—NH—$R^6$ or —NH—$SO_2$—$R^7$, wherein $R^5$ denotes $(C_1-C_6)$-alkyl, which can be substituted by hydroxyl, $(C_1-C_4)$-alkoxy, phenyl or 5- or 6-membered heteroaryl, or phenyl,
    wherein phenyl and heteroaryl in their turn can in each case be substituted once to three times in an identical or different manner by halogen, cyano, $(C_1-C_4)$-alkyl, hydroxyl, $(C_1-C_4)$-alkoxy, trifluoromethyl or trifluoromethoxy,
  $R^6$ denotes $(C_1-C_6)$-alkyl, which can be substituted by hydroxyl or $(C_1-C_4)$-alkoxy,
  and
  $R^7$ denotes $(C_1-C_6)$-alkyl,
and
$R^4$ denotes hydrogen or $(C_1-C_6)$-alkyl, which can be substituted by hydroxyl, $(C_1-C_4)$-alkoxy or phenyl,
    wherein phenyl in its turn can be substituted by halogen, cyano, $(C_1-C_4)$-alkyl, $(C_1-C_4)$-alkoxy, trifluoromethyl or trifluoromethoxy,
$R^2$ represents a substituent chosen from the series consisting of halogen, cyano, nitro, $(C_1-C_6)$-alkyl, trifluoromethyl, hydroxyl, $(C_1-C_6)$-alkoxy, trifluoromethoxy, amino, hydroxycarbonyl and —C(=O)—NH—$R^8$, wherein $(C_1-C_6)$-alkyl and $(C_1-C_6)$-alkoxy in their turn can be substituted by hydroxyl and
  $R^8$ denotes hydrogen or $(C_1-C_4)$-alkyl,
m represents the number 0, 1 or 2,
n represents the number 0, 1, 2 or 3,
  wherein, in the case where $R^1$ or $R^2$ occur several times, their meanings can in each case be identical or different,
and
$R^3$ represents hydrogen, $(C_1-C_6)$-alkyl or $(C_3-C_7)$-cycloalkyl, and their salts, solvates and solvates of the salts.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

The compounds according to the invention can exist in stereoisomeric forms (enantiomers, diastereomers), depending on their structure. The invention therefore includes the enantiomers or diastereomers and their particular mixtures. The stereoisomerically uniform constituents can be isolated from such mixtures of enantiomers and/or diastereomers in a known manner.

If the compounds according to the invention can occur in tautomeric forms, the present invention includes all the tautomeric forms.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The present invention moreover also includes prodrugs of the compounds according to the invention. The term "prodrugs" includes compounds which themselves can be biologically active or inactive, but are converted (for example metabolically or hydrolytically) into compounds according to the invention during their dwell time in the body.

In the context of the present invention, the substituents have the following meaning, unless specified otherwise:

$(C_1-C_6)$-Alkyl and $(C_1-C_4)$-alkyl in the context of the invention represent a straight-chain or branched alkyl radical having 1 to 6 or, respectively, 1 to 4 carbon atoms. A straight-chain or branched alkyl radical having 1 to 4 carbon atoms is preferred. There may be mentioned by way of example and preferably: methyl, ethyl, n-propyl, isopropyl, n-butyl, isobutyl, sec-butyl, tert-butyl, 1-ethylpropyl, n-pentyl and n-hexyl.

$(C_3-C_7)$-Cycloalkyl and $(C_3-C_6)$-cycloalkyl in the context of the invention represent a saturated monocyclic cycloalkyl group having 3 to 7 or, respectively, 3 to 6 carbon atoms. A cycloalkyl radical having 3 to 6 carbon atoms is preferred. There may be mentioned by way of example and preferably: cyclopropyl, cyclobutyl, cyclopentyl, cyclohexyl and cycloheptyl.

$(C_1-C_6)$-Alkoxy and $(C_1-C_4)$-alkoxy in the context of the invention represent a straight-chain or branched alkoxy radical having 2 to 6 or, respectively, 1 to 4 carbon atoms. A straight-chain or branched alkoxy radical having 1 to 4 carbon atoms is preferred. There may be mentioned by way of example and preferably: methoxy, ethoxy, n-propoxy, isopropoxy, n-butoxy and tert-butoxy.

$(C_1-C_6)$-Alkoxycarbonyl and $(C_1-C_4)$-alkoxycarbonyl in the context of the invention represent a straight-chain or branched alkoxy radical having 1 to 6 or, respectively, 1 to 4 carbon atoms which is linked via a carbonyl group. A straight-chain or branched alkoxycarbonyl radical having 1 to 4 carbon atoms is preferred. There may be mentioned by way of example and preferably: methoxycarbonyl, ethoxycarbonyl, n-propoxycarbonyl, isopropoxycarbonyl and tert-butoxycarbonyl.

Mono-$(C_1-C_4)$-alkylamino in the context of the invention represents an amino group with a straight-chain or branched alkyl substituent which contains 1 to 4 carbon atoms. There may be mentioned by way of example and preferably: methylamino, ethylamino, n-propylamino, isopropylamino, n-butylamino and tert-butylamino.

Di-$(C_1-C_4)$-alkylamino in the context of the invention represents an amino group with two identical or different straight-chain or branched alkyl substituents, each of which contains 1 to 4 carbon atoms. There may be mentioned by way of example and preferably: N,N-dimethylamino, N,N-diethylamino, N-ethyl-N-methylamino, N-methyl-N-n-propylamino, N-isopropyl-N-methylamino, N,N-diisopropylamino, N-n-butyl-N-methylamino, N-tert-butyl-N-methylamino.

5- or 6-membered heteroaryl in the context of the invention represents an aromatic heterocyclic radical (heteroaromatic) having a total of 5 or 6 ring atoms and up to three identical or different ring hetero atoms from the series consisting of N, O and/or S which is linked via a ring carbon atom or optionally a ring nitrogen atom. There may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl. A 5-membered heteroaryl radical having up to two ring hetero atoms from the series consisting of N, O and/or S is preferred, such as, for example, furyl, pyrrolyl, thienyl, pyrazolyl, imidazolyl, thiazolyl, oxazolyl, isoxazolyl, isothiazolyl.

Halogen in the context of the invention includes fluorine, chlorine, bromine and iodine. Fluorine, chlorine or bromine are preferred.

If radicals in the compounds according to the invention are substituted, the radicals can be mono- or polysubstituted, unless specified otherwise. In the context of the present invention, for all the radicals which occur several times, the meaning thereof is independent of one another. Substitution by one, two or three identical or different substituents is preferred. Substitution by one substituent is very particularly preferred.

Preferred compounds of the formula (I) are those in which
A represents CH or N,
$R^1$ represents a substituent chosen from the series consisting of $(C_1-C_6)$-alkyl, trifluoromethyl, cyano, nitro, hydroxyl, $(C_1-C_6)$-alkoxy, amino, $(C_1-C_6)$-alkoxycarbonyl and hydroxycarbonyl,
$R^2$ represents a substituent chosen from the series consisting of halogen, cyano, nitro, $(C_1-C_6)$-alkyl, trifluoromethyl, hydroxyl, $(C_1-C_6)$-alkoxy, trifluoromethoxy, amino and hydroxycarbonyl, wherein $(C_1-C_6)$-alkyl and $(C_1-C_6)$-alkoxy in their turn can be substituted by hydroxyl, m represents the number 0, 1 or 2, n represents the number 0, 1, 2 or 3, wherein, in the case where $R^1$ or $R^2$ occur several times, their meanings can in each case be identical or different, and $R^3$ represents hydrogen, $(C_1-C_6)$-alkyl or $(C_3-C_7)$-cycloalkyl, and their salts, solvates and solvates of the salts.

Compounds of the formula (I) which are likewise preferred are those in which

A represents CH, $R^1$ represents a substituent chosen from the series consisting of $(C_1-C_6)$-alkyl, fluorine, chlorine, bromine and —C(=O)—NH—$R^4$, wherein $(C_1-C_6)$-alkyl in its turn can be substituted by hydroxyl, $(C_1-C_4)$-alkoxy, amino, mono-$(C_1-C_4)$-alkylamino, di-$(C_1-C_4)$-alkylamino or a group of the formula —NH—C(=O)—$R^5$, —NH—C(=O)—NH—$R^6$ or —NH—SO$_2$—$R^7$, wherein $R^5$ denotes $(C_1-C_6)$-alkyl, which can be substituted by hydroxyl, methoxy, ethoxy, phenyl or 5-membered heteroaryl, or phenyl, wherein phenyl and heteroaryl in their turn can in each case be substituted once to three times in an identical or different manner by fluorine, chlorine, bromine, cyano, methyl, hydroxyl, methoxy, ethoxy, trifluoromethyl or trifluoromethoxy, and $R^6$ and $R^7$ independently of one another denote $(C_1-C_6)$-alkyl, and $R^4$ denotes $(C_1-C_6)$-alkyl, which can be substituted by hydroxyl, methoxy, ethoxy or phenyl, wherein phenyl in its turn can be substituted by fluorine, chlorine, bromine, cyano, methyl, methoxy, ethoxy, trifluoromethyl or trifluoromethoxy, $R^2$ represents a substituent chosen from the series consisting of fluorine, chlorine, bromine, cyano, $(C_1-C_6)$-alkyl, trifluoromethyl, hydroxycarbonyl and —C(=O)—NH—$R^8$, wherein $(C_1-C_6)$-alkyl in its turn can be substituted by hydroxyl and $R^8$ denotes $(C_1-C_4)$-alkyl, m represents the number 0, 1 or 2, n represents the number 0, 1 or 2, wherein in the case where $R^1$ or $R^2$ occur several times, their meanings can in each case be identical or different, and $R^3$ represents hydrogen, and their salts, solvates and solvates of the salts.

Compounds of the formula (I) which are particularly preferred are those in which A represents CH, $R^1$ represents a substituent chosen from the series consisting of $(C_1-C_4)$-alkyl, trifluoromethyl, nitro, $(C_1-C_4)$-alkoxy, amino and $(C_1-C_4)$-alkoxycarbonyl, $R^2$ represents a substituent chosen from the series consisting of chorine, bromine, cyano, $(C_1-C_4)$-alkyl, trifluoromethyl, hydroxyl, $(C_1-C_4)$-alkoxy, trifluoromethoxy and amino, wherein $(C_1-C_4)$-alkyl and $(C_1-C_4)$-alkoxy in their turn can be substituted by hydroxyl, m represents the number 0 or 1, n represents the number 0, 1, 2 or 3, wherein, in the case where $R^2$ occurs several times, its meanings can be identical or different, and $R^3$ represents hydrogen or methyl, and their salts, solvates and solvates of the salts.

Compounds of the formula (I) which are likewise particularly preferred are those in which A represents CH, $R^1$ represents a substituent chosen from the series consisting of $(C_1-C_4)$-alkyl, fluorine, chlorine, bromine and —C(=O)—NH—$R^4$, wherein $(C_1-C_4)$-alkyl in its turn can be substituted by hydroxyl, amino or a group of the formula —NH—C(=O)—$R^5$ or —NH—C(=O)—NH—$R^6$, wherein $R^5$ denotes $(C_1-C_4)$-alkyl, which can be substituted by phenyl or pyrazolyl, or phenyl, wherein phenyl and pyrazolyl in their turn can in each case be substituted once to three times in an identical or different manner by fluorine, chlorine, methyl or trifluoromethyl, and $R^6$ denotes $(C_1-C_4)$-alkyl, and $R^4$ denotes $(C_1-C_4)$-alkyl, which can be substituted by phenyl, $R^2$ represents a substituent chosen from the series consisting of chlorine, bromine, cyano, $(C_1-C_4)$-alkyl and trifluoromethyl, wherein $(C_1-C_4)$-alkyl in its turn can be substituted by hydroxyl, m represents the number 0, 1 or 2, n represents the number 0, 1 or 2, wherein, in the case where $R^1$ or $R^2$ occur several times, their meanings can in each case be identical or different, and $R^3$ represents hydrogen, and their salts, solvates and solvates of the salts.

Compounds which are of particular importance are those of the formula (I-A)

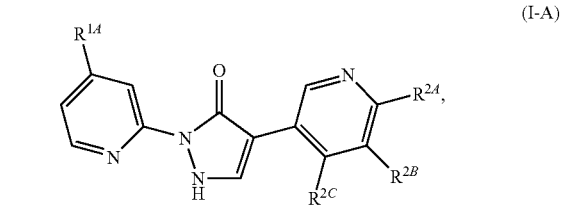

(I-A)

in which

R$^{1A}$ represents hydrogen, methyl or trifluoromethyl
and

R$^{2A}$, R$^{2B}$ and R$^{2C}$ are identical or different and independently of one another represent hydrogen, chlorine, bromine, cyano, methyl, hydroxymethyl, methoxy or ethoxy, and their salts, solvates and solvates of the salts.

Compounds which are of particular importance are likewise those of the formula (I-B)

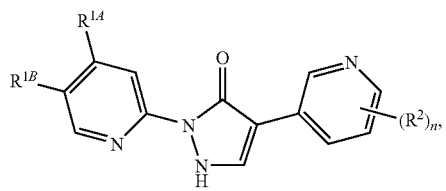

(I-B)

in which

R$^{1A}$ and R$^{1B}$ are identical or different and independently of one another represent hydrogen, fluorine, chlorine, (C$_1$-C$_4$)-alkyl or —C(=O)—NH—R$^4$, wherein (C$_1$-C$_4$)-alkyl in its turn can be substituted by hydroxyl, amino or a group of the formula —NH—C(=O)—R$^5$, wherein R$^5$ denotes (C$_1$-C$_4$)-alkyl, which can be substituted by phenyl or pyrazolyl, or phenyl, wherein phenyl and pyrazolyl in their turn can in each case be substituted once to three times in an identical or different manner by fluorine, chlorine, methyl or trifluoromethyl, and R$^4$ denotes (C$_1$-C$_4$)-alkyl, which can be substituted by phenyl, R$^2$ represents a substituent chosen from the series consisting of chlorine, bromine, cyano, methyl, hydroxymethyl or trifluoromethyl and n represents the number 0, 1 or 2, wherein in the case where R$^2$ occurs several times, its meanings can be identical or different, and their salts, solvates and solvates of the salts.

The radical definitions given in detail in the particular combinations or preferred combinations of radicals are also replaced as desired by radical definitions of other combinations, independently of the particular radical combinations given.

Combinations of two or more of the abovementioned preferred ranges are very particularly preferred.

The 1,2-dihydropyrazol-3-one derivatives of the formula (I) according to the invention can also be in the tautomeric 1H-pyrazol-5-ol form (I') (see following equation 1); the two tautomeric forms are expressly included in the present invention.

Equation 1

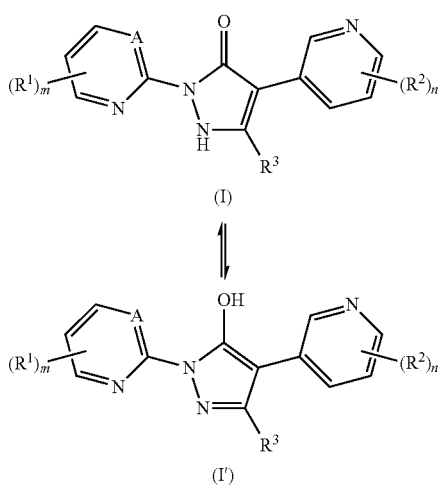

The invention also provides a process for the preparation of the compounds of the formula (I) according to the invention, characterized in that compounds of the formula (II)

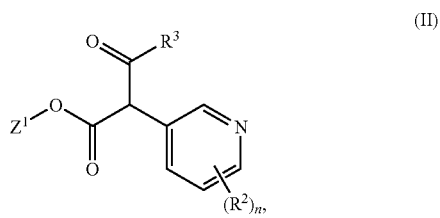

in which R$^2$, R$^3$ and n have the abovementioned meanings and Z$^1$ represents methyl or ethyl, are reacted in an inert solvent, optionally in the presence of an acid, with a compound of the formula (III)

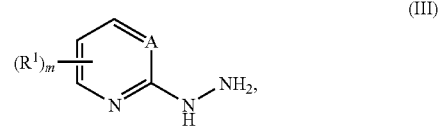

in which A, R$^1$ and m have the abovementioned meanings, to give compounds of the formula (IV)

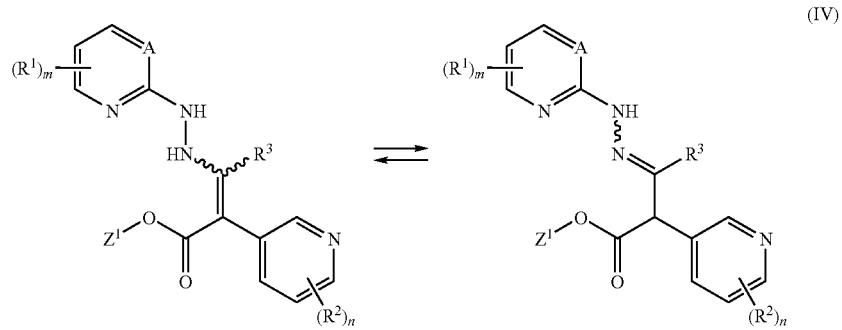

in which $Z^1$, A, $R^1$, $R^2$, $R^3$, m and n have the abovementioned meanings,
and these are then cyclized in an inert solvent in the presence of a base
and the compounds of the formula (I) are optionally converted with the corresponding (i) solvents and/or (ii) bases or acids into their solvates, salts and/or solvates of the salts.

The compounds of the formula (I) according to the invention in which $R^3$ represents hydrogen can also be prepared by a process in which compounds of the formula (V)

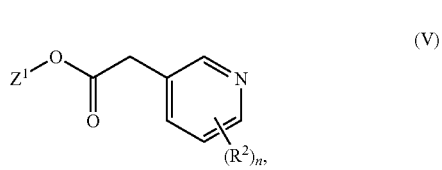

in which
$Z^2$ represents methyl or ethyl,
to give compounds of the formula (VII)

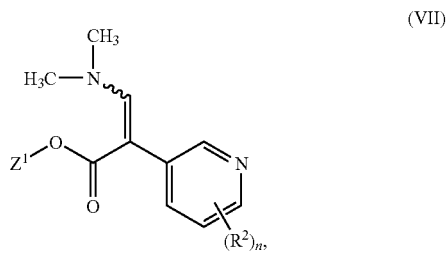

in which $Z^1$, $R^2$ and n have the abovementioned meanings,
which are then reacted in the presence of an acid with a compound of the formula (III) to give compounds of the formula (IV-A)

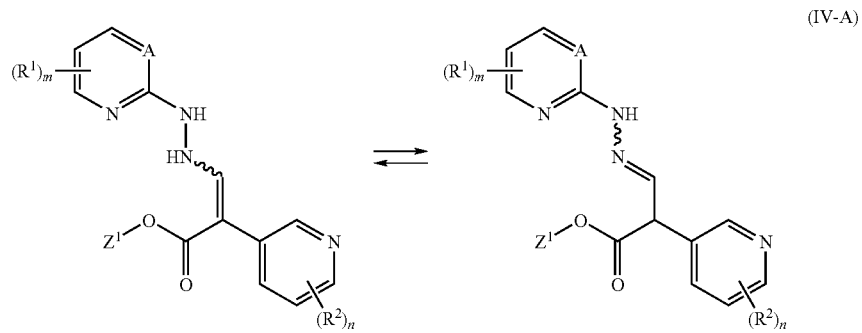

in which $Z^1$, $R^2$ and n and m have the abovementioned meanings,
are subjected to a condensation reaction with a compound of the formula (VI)

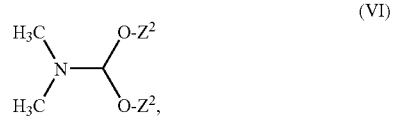

in which $Z^1$, A, $R^1$, $R^2$, m and n have the abovementioned meanings,
and these are then cyclized in an inert solvent in the presence of a base.

The compounds according to the invention can optionally also be prepared by further conversions of functional groups of individual substituents, in particular those listed under $R^1$ and $R^2$, starting from the compounds of the formula (I) obtained by the above process. These conversions are carried out by conventional methods and include, for example, reactions such as nucleophilic or electrophilic substitution, oxidation, reduction, hydrogenation, esterification, ester cleavage, etherification, ether cleavage, formation of carboxamides, sulfonamides and ureas, and the introduction and removal of temporary protective groups.

Suitable inert solvents for the process steps (II)+(III)→(IV), (IV)→(I) and (IV-A)→(I) are, in particular, alcohols, such as methanol, ethanol, n-propanol, iso-propanol, n-butanol or tert-butanol. Ethanol is preferably used.

The process step (II)+(III)→(IV) can optionally advantageously be carried out with the addition of an acid. Conventional inorganic or organic acids are suitable for this, such as, for example, hydrogen chloride, acetic acid, trifluoroacetic acid, methanesulfonic acid or para-toluenesulfonic acid. Acetic acid is preferably used.

The reaction (II)+(III)→(IV) is in general carried out in a temperature range of from 0° C. to +100° C., preferably from +10° C. to +40° C.

Conventional inorganic or organic bases are suitable as the base for the cyclization step (IV)→(I) or (IV-A)→(I). These include, in particular, alkali metal hydroxides, such as, for example, sodium or potassium hydroxide, alkali metal or alkaline earth metal carbonates, such as sodium, potassium, calcium or cesium carbonate, alkali metal alcoholates, such as sodium or potassium methanolate, sodium or potassium ethanolate or sodium or potassium tert-butylate, or alkali metal hydrides, such as sodium hydride. Sodium ethanolate is preferably used.

The reaction (IV)→(I) or (IV-A)→(I) is in general carried out in a temperature range of from 0° C. to +60° C., preferably from 0° C. to +30° C.

The process sequence (II)+(III)→(IV)→(I) can be carried out under a two-stage reaction procedure or also as a one-pot reaction, without isolation of the intermediate stage (IV).

The process step (V)+(VI)→(VII) is preferably carried out without a solvent in the presence of an excess of (VI) under microwave irradiation. The reaction is in general carried out in a temperature range of from +20° C. to +150° C., preferably from +80° C. to 120° C. [cf. also J. P. Bazureau et al., *Synthesis* 1998, 967; ibid. 2001 (4), 581].

The process step (VII)+(III)→(IV-A) is advantageously carried out with the addition of an acid. Conventional inorganic or organic acids are suitable for this, such as, for example, hydrogen chloride, acetic acid, trifluoroacetic acid, methanesulfonic acid or para-toluenesulfonic acid. Acetic acid is preferably used. Inert solvents which can be employed for this process step are alcohols, such as methanol, ethanol, n-propanol, iso-propanol, n-butanol or tert-butanol. The reaction is particularly preferably carried out in acetic acid itself, without addition of a further solvent.

The reaction (VII)+(III)→(IV-A) is in general carried out in a temperature range of from 0° C. to +60° C., preferably from +10° C. to +30° C.

All the process steps can be carried out under normal, increased or reduced pressure (e.g. from 0.5 to 5 bar). In general, normal pressure is applied.

The compounds of the formula (II) can be prepared by methods known from the literature for C-acylation of carboxylic acid esters from compounds of the formula (V). The compounds of the formulae (III), (V) and (VI) are commercially obtainable or known from the literature or can be prepared analogously to processes known from the literature.

The preparation of the compounds according to the invention can be illustrated by the following synthesis equations 2-4:

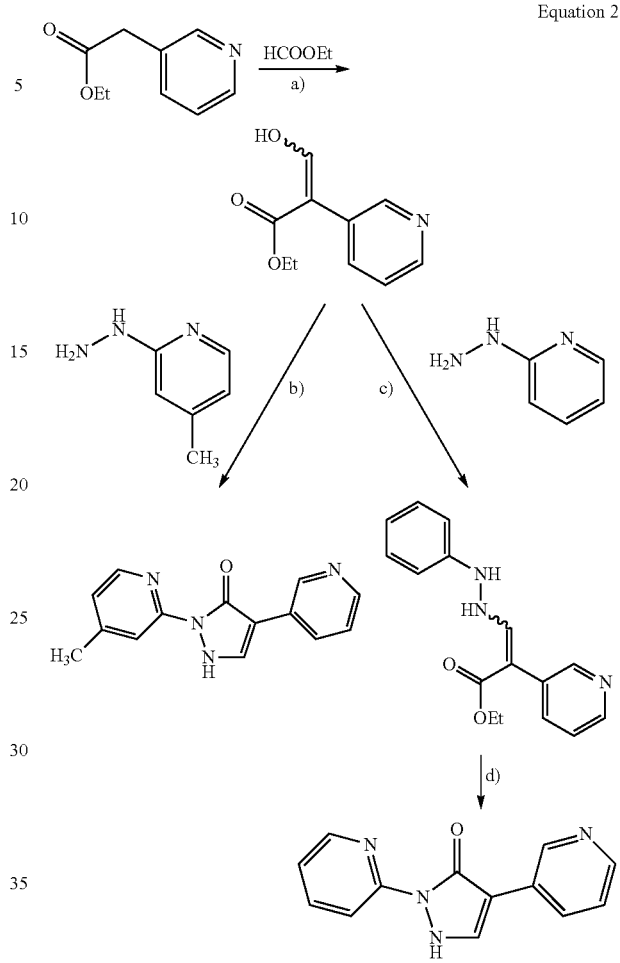

Equation 2

[a]: NaH, 18-crown-6, toluene, 1 h RT → 1 h 90° C.;
b): 1. ethanol, 16 h RT; 2. NaOEt, ethanol, 30 min RT;
c): ethanol, 1 d RT;
d): NaOEt, ethanol, 1 h RT].

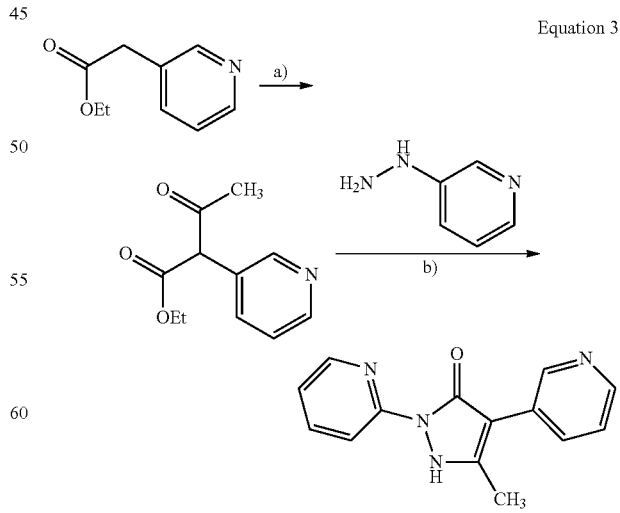

Equation 3

[a]: 1. LiHDMS, THF, -78° C. → 1 h 0° C.; 2. acetic anhydride, -78° C.; 3. 36 h RT;
b): glacial acetic acid, ethanol, 16 h RT; 2. NaOEt, ethanol, 30 min RT].

Equation 4

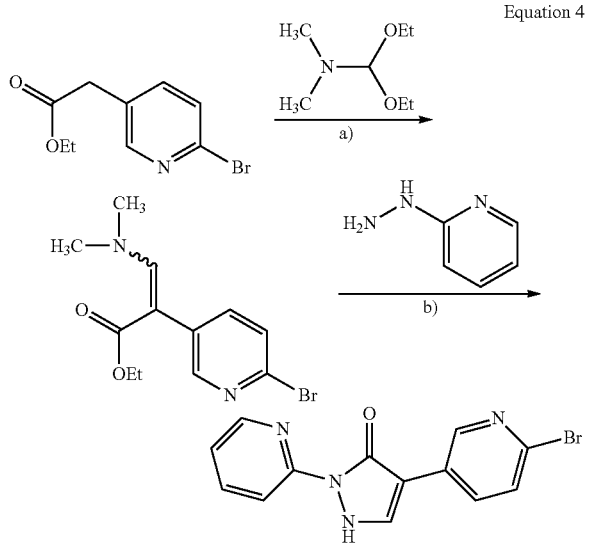

[a]: microwave irradiation, 1 h 100° C.; b): 1. glacial acetic acid, 2 h RT; 2. working up, aq. NaHCO₃; 3. NaOEt, ethanol, 30 min 5° C.; alternatively
b): cat. camphor-10-sulfonic acid, ethanol, 78° C., 12-18 h].

The compounds according to the invention show an unforeseeable, valuable pharmacological action spectrum. They are therefore suitable for use as medicaments for treatment and/or prophylaxis of diseases in humans and animals.

The compounds according to the invention are distinguished as specific inhibitors of HIF prolyl 4-hydroxylases.

On the basis of the pharmacological properties, the compounds according to the invention can be employed for treatment and/or prophylaxis of cardiovascular diseases, in particular cardiac insufficiency, coronary heart disease, angina pectoris, myocardial infarction, stroke, arteriosclerosis, essential, pulmonary and malignant hypertension and peripheral arterial occlusive disease. The compounds are furthermore suitable for treatment and/or prophylaxis of blood formation disorders, such as e.g. idiopathic anemias, renal anemia, anemias accompanying a tumor disease, an infection or another inflammatory disease, such as e.g. rheumatoid arthritis.

The compounds are furthermore suitable for increasing the hematocrit with the aim of obtaining blood for autodonation of blood before operations.

The compounds according to the invention can moreover be used for treatment and/or prophylaxis of operation-related states of ischaemia and consecutive symptoms thereof after surgical interventions, in particular interventions on the heart using a heart-lung machine (e.g. bypass operations, heart valve implants), interventions on the carotid arteries, interventions on the aorta and interventions with instrumental opening or penetration of the skull cap. The compounds are furthermore suitable for general treatment and/or prophylaxis in the event of surgical interventions with the aim of accelerating wound healing and shortening the reconvalescence time.

The compounds can furthermore be employed for treatment and/or prophylaxis of cancer and for treatment and/or prophylaxis of an impairment in the state of health occurring in the course of treatment of cancer, in particular after therapy with cytostatics, antibiotics and irradiations.

The compounds are furthermore suitable for treatment and/or prophylaxis of diseases of the rheumatic type and other diseases forms to be counted as autoimmune diseases, and in particular for treatment and/or prophylaxis of an impairment in the state of health occurring in the course of medicamentous treatment of such diseases.

The compounds according to the invention can moreover be employed for treatment and/or prophylaxis of diseases of the eye (e.g. glaucoma), the brain (e.g. Parkinson's disease, Alzheimer's disease, dementia, chronic pain sensation), of chronic kidney diseases, renal insufficiency and acute renal failure and for promoting wound healing.

The compounds are moreover suitable for treatment and/or prophylaxis of general physical weakness, up to cachexia, in particular occurring to an increased extent at a more elderly age.

The compounds are furthermore suitable for treatment and/or prophylaxis of sexual dysfunction.

The compounds are moreover suitable for treatment and/or prophylaxis of diabetes mellitus and its consecutive symptoms, such as e.g. diabetic macro- and microangiopathy, diabetic nephropathy and neuropathy.

The compounds according to the invention are moreover suitable for treatment and/or prophylaxis of fibrotic diseases e.g. of the heart, the lungs and the liver.

The present invention moreover provides the use of the compounds according to the invention for treatment and/or prevention of diseases, in particular the abovementioned diseases.

The present invention moreover provides the use of the compounds according to the invention for the preparation of a medicament for treatment and/or prevention of diseases, in particular the abovementioned diseases.

The present invention moreover provides a method for treatment and/or prevention of diseases, in particular the abovementioned diseases, using an active amount of at least one of the compounds according to the invention.

The compounds according to the invention can be employed by themselves or, if required, in combination with other active compounds. The present invention moreover provides medicaments comprising at least one of the compounds according to the invention and one or more further active compounds, in particular for treatment and/or prevention of the abovementioned diseases. Suitable active compounds in the combination which may be mentioned by way of example and preferably are: ACE inhibitors, angiotensin II receptor antagonists, beta receptor blockers, mineralocorticoid receptor antagonists, aspirin, diuretics, iron supplements, vitamin B12 and folic acid supplements, calcium antagonists, statins and digitalis (digoxin) derivatives.

The present invention moreover provides medicaments which comprise at least one compound according to the invention, conventionally together with one or more inert, non-toxic, pharmaceutically suitable auxiliary substances, and the use thereof for the abovementioned purposes.

The compounds according to the invention can act systemically and/or locally. They can be administered in a suitable manner for this purpose, such as e.g. orally, parenterally, pulmonally, nasally, sublingually, lingually, buccally, rectally, dermally, transdermally, conjunctivally, otically or as an implant or stent.

The compounds according to the invention can be administered in suitable administration forms for these administration routes.

Administration forms which function according to the prior art, release the compounds according to the invention rapidly and/or in a modified manner and comprise the compounds according to the invention in crystalline and/or amorphized and/or dissolved form are suitable for oral administration, such as e.g. tablets (non-coated or coated tables, for example coatings which are resistant to gastric juice or dissolve in a delayed manner or are insoluble and control the release of the compound according to the invention), tablets or films/oblates, films/lyophilisates or capsules which disintegrate rapidly in the oral cavity (for example hard or soft gelatin capsules), sugar-coated tablets, granules, pellets, powders, emulsions, suspensions, aerosols or solutions.

Parenteral administration can be effected with bypassing of an absorption step (e.g. intravenously, intraarterially, intracardially, intraspinally or intralumbally) or with inclusion of an absorption (e.g. intramuscularly, subcutaneously, intracutaneously, percutaneously or intraperitoneally). Administration forms which are suitable for parenteral administration are, inter alia, injection and infusion formulations in the form of solutions, suspensions, emulsions, lyophilisates or sterile powders.

For the other administration routes e.g. inhalation medicament forms (inter alia powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents are suitable.

Oral or parenteral administration are preferred, in particular oral administration.

The compounds according to the invention can be converted into the administration forms mentioned. This can be effected in a manner known per se by mixing with inert, non-toxic, pharmaceutically suitable auxiliary substances. These auxiliary substances include inter alia carrier substances (for example microcrystalline cellulose, lactose, mannitol), solvents (e.g. liquid polyethylene glycols), emulsifiers and dispersing or wetting agents (for example sodium dodecyl sulfate, polyoxysorbitan oleate), binders (for example polyvinylpyrrolidone), synthetic and natural polymers (for example albumin), stabilizers (e.g. antioxidants, such as, for example, ascorbic acid), dyestuffs (e.g. inorganic pigments, such as e.g. iron oxides) and flavor and/or smell correctants.

In general, it has proved advantageous in the case of parenteral administration to administer amounts of from about 0.001 to 1 mg/kg, preferably about 0.01 to 0.5 mg/kg of body weight to achieve effective results. In the case of oral administration the dosage is about 0.01 to 100 mg/kg, preferably about 0.01 to 20 mg/kg and very particularly preferably 0.1 to 10 mg/kg of body weight.

Nevertheless it may be necessary to deviate from the amounts mentioned, and in particular depending on the body weight, administration route, individual behavior towards the active compound, nature of the formulation and point of time or interval at which administration takes place. Thus in some cases it may be sufficient to manage with less than the abovementioned minimum amount, while in other cases the upper limit mentioned must be exceeded. In the case where relatively large amounts are administered, it may be advisable to distribute these into several individual doses over the day.

The following embodiment examples illustrate the invention. The inventions is not limited to the examples.

The percentage data in the following tests and examples are percentages by weight, unless stated otherwise; parts are parts by weight. The solvent ratios, dilution ratios and concentration data of liquid/liquid solutions in each case relate to the volume.

A. EXAMPLES

Abbreviations and Acronyms
aq. aqueous solution
cat. catalytic
d day(s)
DCI direct chemical ionization (in MS)
DMF dimethylformamide
DMSO dimethylsulfoxide
of th. of theory (yield)
EI electron impact ionization (in MS)
ESI electrospray ionization (in MS)
Et ethyl
GC-MS gas chromatography-coupled mass spectroscopy
h hour(s)
HPLC high pressure, high performance liquid chromatography
conc. concentrated
LC-MS liquid chromatography-coupled mass spectroscopy
LiHMDS lithium hexamethyldisilazide
min minute(s)
MS mass spectroscopy
MTBE methyl tert-butyl ether
NMR nuclear magnetic resonance spectroscopy
$R_t$ retention time (in HPLC)
RT room temperature
TFA trifluoroacetic acid
THF tetrahydrofuran
LC-MS, HPLC and GC-MS methods:
Method 1:
Instrument: Micromass Platform LCZ with HPLC Agilent Series 1100; column: Thermo Hypersil GOLD 3μ, 20 mm×4 mm; eluent A: 1 l water+0.5 ml 50% strength formic acid, eluent B: 1 l acetonitrile+0.5 ml 50% strength formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.
Method 2:
Instrument: Micromass Platform LCZ with HPLC Agilent Series 1100; column: Thermo HyPURITY Aquastar 3μ, 50 mm×2.1 mm; eluent A: 1 l water+0.5 ml 50% strength formic acid, eluent B: 1 l acetonitrile+0.5 ml 50% strength formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.
Method 3:
Instrument: Micromass Quattro LCZ with HPLC Agilent Series 1100; column: Phenomenex Synergi 2μ Hydro-RP Mercury 20 mm×4 mm; eluent A: 1 l water+0.5 ml 50% strength formic acid, eluent B: 1 l acetonitrile+0.5 ml 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.
Method 4:
Apparatus type MS: Micromass ZQ; apparatus type HPLC: Waters Alliance 2795; column: Phenomenex Synergi 2μ Hydro-RP Mercury 20 mm×4 mm; eluent A: 1 l water+0.5 ml 50% strength formic acid, eluent B: 1 l acetonitrile+0.5 ml 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 5:
Apparatus type MS: Micromass ZQ; apparatus type HPLC: HP 1100 Series; UV DAD; column: Phenomenex Synergi 2μ Hydro-RP Mercury 20 mm×4 mm; eluent A: 1 l water+0.5 ml 50% strength formic acid, eluent B: 1 l acetonitrile+0.5 ml 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 6:

Instrument: HP 1100 Series with DAD detection; column: Kromasil 100 RP-18, 60 mm×2.1 mm, 3.5 µm; eluent A: 5 ml HClO$_4$ (70% strength)/1 water, eluent B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.

Method 7:

Instrument: Micromass GCT, GC6890; column: Restek RTX-35MS, 30 m×250 µm×0.25 µm; constant flow rate with helium: 0.88 ml/min; oven: 60° C.; inlet: 250° C.; gradient: 60° C. (hold 0.30 min), 50° C./min→120° C., 16° C./min→250° C., 30° C./min→300° C. (hold 1.7 min).

Method 8:

Instrument MS: Waters ZQ 2000; instrument HPLC: Agilent 1100, 2-column circuit; autosampler: HTC PAL; column: YMC-ODS-AQ, 50 mm×4.6 mm, 3.0 µm; eluent A: water+0.1% formic acid, eluent B: acetonitrile+0.1% formic acid; gradient: 0.0 min 100% A→0.2 min 95% A→1.8 min 25% A→1.9 min 10% A→2.0 min 5% A→3.2 min 5% A→3.21 min 100% A→3.35 min 100% A; oven: 40° C.; flow rate: 3.0 ml/min; UV detection: 210 nm.

Starting Compounds and Intermediates:

Example 1A

2-Hydrazino-4-methylpyridine

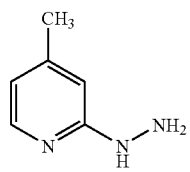

3.33 g (30.0 mmol) 2-fluoro-4-methylpyridine are initially introduced into 40 ml 2-ethoxyethanol, 14.6 ml (15.0 g, 300 mmol) hydrazine hydrate are added to the solution and the mixture is stirred at the boil (150° C. bath temperature) for 16 h. The reaction solution is concentrated on a rotary evaporator, the residue is introduced on to 100 ml water and the mixture is extracted with ethyl acetate (three times with 100 ml each time). The combined organic phases are dried over sodium sulfate, filtered and concentrated. The residue obtained is dried in vacuo.

Yield: 1.90 g (51% of th.)

$^1$H-NMR (400 MHz, DMSO-d$_6$): δ=7.83 (d, 1H), 7.22 (s, 1H), 6.51 (s, 1H), 6.38 (d, 1H), 4.04 (s, 2H), 2.17 (s, 3H)

LC-MS (Method 1): R$_t$=0.80 min; MS (ESIpos): m/z=124 [M+H]$^+$.

Example 2A

3-Hydroxy-2-pyridin-3-yl-acrylic acid ethyl ester

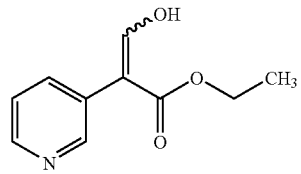

1.65 g (10.0 mmol) 3-pyridylacetic acid ethyl ester are initially introduced into 20 ml anhydrous toluene under argon. 410 mg (10.3 mmol) sodium hydride suspension (60% strength in paraffin oil) and 130 mg (0.50 mmol) 18-crown-6 are added in portions to the solution and the mixture is stirred at RT for 30 min and then at 85° C. (bath temperature) for 30 min. After this time, the mixture is cooled and 1.48 g (20.0 mol) formic acid ethyl ester are added dropwise at approx. 20° C. The mixture is stirred first at RT for 60 min and then at 90° C. (bath temperature) for 60 min. After cooling, the reaction solution is introduced on to approx. 50 ml saturated ammonium chloride solution and extracted with ethyl acetate (five times with 40 ml each time). The combined organic phases are washed with 50 ml saturated sodium chloride solution, dried over sodium sulfate, filtered and concentrated. The solid obtained is washed with pentane and dried in vacuo.

Yield: 1.3 g (67% of th.)

$^1$H-NMR (400 MHz, DMSO-d$_6$): δ=11.38 (br. s, 1H), 8.50 (d, 1H), 8.39 (dd, 1H), 7.97 (s, 1H), 7.71 (d, 1H), 7.35 (dd, 1H), 4.12 (q, 2H), 1.97 (t, 3H).

MS (DCI): m/z=194 [M+H]$^+$.

Example 3A

2-Pyridin-3-yl-3-(pyridin-2-ylhydrazono)propionic acid ethyl ester

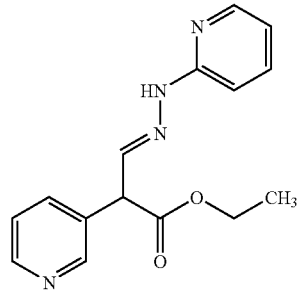

2.90 g (15.0 mmol) of the compound from Example 2A and 1.72 g (15.8 mmol) 2-pyridylhydrazine are dissolved in 75 ml ethanol and the mixture is stirred at RT for 4 d. The reaction mixture is freed from the solvent on a rotary evaporator and the residue is chromatographed over silica gel 60 (mobile phase: methylene chloride→methylene chloride/methanol 10:1→methylene chloride/methanol 2:1). The product fractions are combined and the solvent is removed on a rotary evaporator. After drying in vacuo, 3.95 g (93% of th.) of the title compound are obtained.

Example 4A (6-Bromopyridin-3-yl)methanol

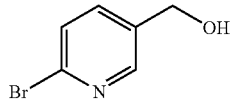

1.34 ml (1.34 mmol) of a 1 M solution of lithium aluminum hydride in THF are initially introduced into 5 ml dry THF under argon, and a solution of 500 mg (2.69 mmol) 6-bromo-3-pyridinecarbaldehyde in 3 ml dry THF is added dropwise at 0° C. The mixture is subsequently stirred at RT for 1 h, 25 ml ethyl acetate are then added, while cooling in an ice bath, and hydrolysis is carried out slowly with 50 ml saturated sodium bicarbonate solution. The aqueous phase is extracted with ethyl acetate (three times with 20 ml each time). The combined organic phases are washed with saturated sodium chloride solution, dried over sodium sulfate, filtered and concentrated on a rotary evaporator. After removal of solvent residues in vacuo, 375 mg (74% of th.) of the title compound are obtained.

LC-MS (Method 3): $R_t$=1.02 min; MS (ESIpos): m/z=189 [M+H]$^+$.

Example 5A (6-Chloro-5-methylpyridin-3-yl)methanol

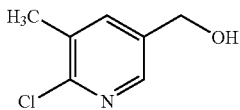

The title compound is obtained by reaction of 3.11 g (20.0 mmol) 6-chloro-5-methylnicotinaldehyde [preparation described in DE 4429465-A1, Example 7] with 1.51 g (40.0 mmol) sodium borohydride in 30 ml water and subsequent extraction of the aqueous phase with methylene chloride. The product obtained after removal of the solvent on a rotary evaporator is dried in vacuo and further used directly.

Example 6A

2-Bromo-5-(chloromethyl)pyridine

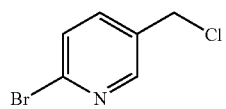

3.69 g (19.7 mmol) of the compound from Example 4A are initially introduced into the reaction vessel under argon and 25 ml thionyl chloride are added dropwise at −60° C. (bath temperature). The mixture is stirred at −60° C. for 1 h. It is concentrated at RT on a rotary evaporator, and 50 ml saturated sodium bicarbonate solution and 50 ml ethyl acetate are added to the residue. The aqueous phase is extracted with ethyl acetate (four times with 25 ml each time). The combined organic phases are dried over sodium sulfate and filtered, the solvent is removed on a rotary evaporator and the residue is dried in vacuo.

Yield: 3.71 g (91% of th.)

LC-MS (Method 1): $R_t$=3.28 min; MS (ESIpos): m/z=208 [M+H]$^+$.

Example 7A

2-Chloro-5-(chloromethyl)-3-methylpyridine

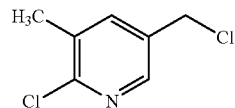

The preparation is carried out analogously to Example 6A from 1.00 g (6.35 mmol) (6-chloro-5-methylpyridin-3-yl)methanol and 5 ml thionyl chloride. 1.26 g of the title compound, which is reacted without further purification, are obtained.

LC-MS (Method 4): $R_t$=1.92 min; MS (ESIpos): m/z=176 [M]$^+$.

Example 8A (6-Bromopyridin-3-yl)acetonitrile

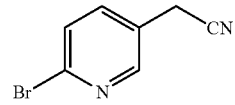

3.75 g (18.2 mmol) of the compound from Example 6A are initially introduced into 20 ml DMF, 979 mg (20.0 mmol) sodium cyanide are added and the mixture is stirred at RT for 2 d. The reaction mixture is introduced on to a mixture of 250 ml saturated ammonium chloride solution and 200 ml ethyl acetate and the aqueous phase is extracted with ethyl acetate (three times with 100 ml each time). The combined organic phases are dried over sodium sulfate, filtered and concentrated and the residue is dried in vacuo. The product obtained in this way is reacted without further purification.

Yield: 3.23 g (90% of th.)

LC-MS (Method 3): $R_t$=1.46 min; MS (ESIpos): m/z=197 [M+H]$^+$.

Example 9A (6-Chloro-5-methylpyridin-3-yl)acetonitrile

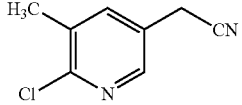

The synthesis is carried out analogously to Example 8A from 1.26 g (7.14 mmol) of the compound from Example 7A. The crude product obtained is purified by chromatography over silica gel 60 (mobile phase: methylene chloride→methylene chloride/methanol 50:1.

Yield: 215 mg (18% of th.)

LC-MS (Method 1): $R_t$=2.95 min; MS (ESIpos): m/z=167 [M+H]$^+$.

Example 10A (2-Chloropyridin-3-yl)acetic acid ethyl ester

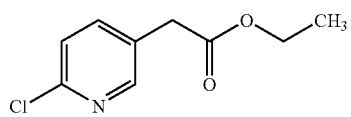

22.0 g (144 mmol) (6-chloropyridin-3-yl)acetonitrile are added to a mixture of 270 ml ethanol and 101 ml conc. sulfuric acid and the mixture is stirred under reflux for 24 h. The reaction mixture is slowly added dropwise, with stirring, to a mixture of 350 g sodium bicarbonate and 1 liter water. The aqueous phase is extracted with methylene chloride (five times with 400 ml each time). The combined organic phases are dried over sodium sulfate, filtered and freed from the solvent on a rotary evaporator. 23.1 g (80% of th.) of the title compound, which is reacted without further purification, are obtained.

$^1$H-NMR (400 MHz, DMSO-d$_6$): δ=8.32 (d, 1H), 7.78 (dd, 1H), 7.49 (d, 1H), 4.10 (q, 2H), 3.77 (s, 2H), 1.19 (t, 3H).

LC-MS (Method 3): $R_t$=1.91 min; MS (ESIpos): m/z=200 [M+H]$^+$.

The compounds listed in Table 1 are obtained in an analogous manner to Example 10A from the corresponding educts:

TABLE 1

| Example no. | Structure | MS (ESI) [M + H]$^+$ | LC-MS $R_t$ [min] (method) | Yield (% of th.) |
|---|---|---|---|---|
| 11A | 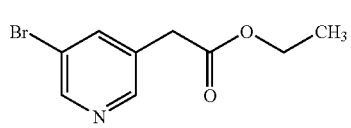 | 246 | 2.02 (5) | 55 |
| 12A | H$_3$C, Cl pyridine ethyl ester structure | 214 | 2.14 (5) | 86 |

Example 13A (5-Bromopyridin-3-yl)acetic acid ethyl ester

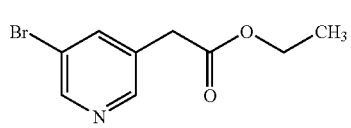

1.00 g (4.63 mmol) (5-bromopyridin-3-yl)acetic acid are initially introduced into 20 ml ethanol, 2 ml conc. sulfuric acid are added and the mixture is stirred under reflux overnight. The reaction solution is introduced on to a mixture of 100 ml saturated sodium bicarbonate solution and 100 ml ethyl acetate, while stirring, and the aqueous phase is extracted with ethyl acetate (three times with 50 ml each time). The combined organic phases are dried over sodium sulfate, filtered and concentrated and the residue is freed from solvent residues overnight in vacuo.

Yield: 1.06 g (94% of th.)

$^1$H-NMR (400 MHz, DMSO-d$_6$): δ 8.61 (d, 1H), 8.48 (d, 1H), 8.01 (dd, 1H), 4.10 (q, 2H), 3.78 (s, 2H), 1.20 (t, 3H).

LC-MS (Method 5): $R_t$=2.06 min; MS (ESIpos): m/z=246 [M+H]$^+$.

Example 14A 2-(6-Bromopyridin-3-yl)-3-(dimethylamino)acrylic acid ethyl ester

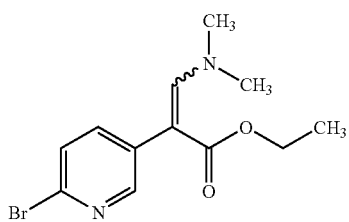

1.30 g (2.98 mmol) of the compound from Example 11A are dissolved in 6 ml dimethylformamide diethyl acetal and the mixture is stirred under microwave irradiation at 100° C. for 60 min. The mixture is concentrated on a rotary evaporator and the residue is chromatographed over silica gel 60 (mobile phase: cyclohexane cyclohexane/ethyl acetate 1:3).

Yield: 854 mg (96% of th.)

$^1$H-NMR (400 MHz, DMSO-d$_6$): δ=8.11 (d, 1H), 7.61 (s, 1H), 7.54 (d, 1H), 7.48 (dd, 1H), 4.01 (q, 2H), 2.70 (br. s, 6H), 1.12 (t, 3H).

MS (DCI, NH$_3$): m/z=316 [M+NH$_4$]$^+$

LC-MS (Method 4): $R_t$=1.88 min; MS (ESIpos): m/z=299 [M+H]$^+$.

The compounds listed in Table 2 are prepared analogously to Example 14A from the corresponding educts:

TABLE 2

| Example no. | Structure | Yield (% of th.) | MS (ESI) [M + H]+; LC-MS R_t [min] (method) | 1H-NMR |
|---|---|---|---|---|
| 15A | 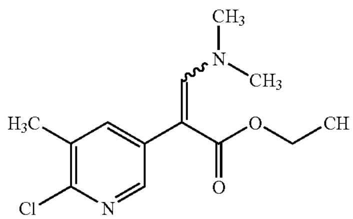 | 70 | m/z = 269; 1.97 min (4) | (400 MHz, DMSO-d_6): δ = 7.97 (d, 1 H), 7.60 (s, 1 H), 7.53 (d, 1 H), 4.00 (q, 2 H), 2.70 (s, 6 H), 2.31 (s, 3 H), 1.12 (t, 3 H). |
| 16A | 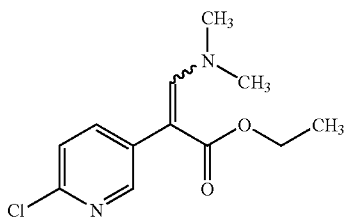 | 90 | m/z = 255; 1.98 min (3) | (300 MHz, DMSO-d_6): δ = 8.13 (d, 1 H), 7.61 (s, 1 H), 7.58 (dd, 1 H), 7.41 (d, 1 H), 4.01 (q, 2 H), 2.70 (s, 6 H), 1.12 (t, 3 H). |
| 17A | 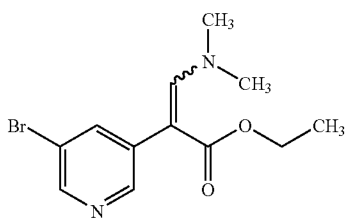 | 80 | m/z = 301; 1.83 min (4) | (300 MHz, DMSO-d_6): δ = 8.49 (d, 1 H), 8.30 (d, 1 H), 7.78 (dd, 1 H), 7.62 (s, 1 H), 4.02 (q, 2 H), 2.71 (s, 6 H), 1.13 (t, 3 H). |

Example 18A

3-Oxo-2-pyridin-3-yl-butanoic acid ethyl ester

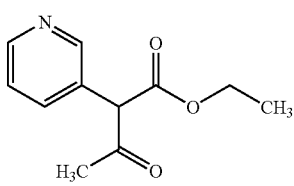

500 mg (3.0 mmol) ethyl-pyridine 3-acetate are initially introduced into 5 ml anhydrous THF under argon, and a solution of lithium hexamethyldisilazide (6.7 ml, 1 M in THF) is added dropwise at −78° C. After 15 min, the mixture is warmed to 0° C., subsequently stirred for 1 h and cooled again to −78° C. After addition of 340 mg (3.3 mmol) acetic anhydride, the mixture is stirred at RT for 36 h. Aqueous ammonium chloride solution is added, the mixture is extracted with methylene chloride and the organic phase is dried over magnesium sulfate and concentrated in vacuo. 488 mg of the title compound, which is reacted without further purification, are obtained with a purity of 70%.

LC-MS (Method 1): R_t=2.24 min; MS (ESIpos): m/z=208 [M+H]+.

Example 19A (5-Methylpyridin-3-yl)acetonitrile

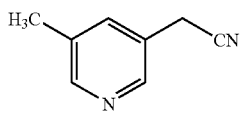

The preparation of the title compound is described in DE 2 854 210-C2 (Table 2, Example 37).

Example 20A 5-(Cyanomethyl)pyridine-2-carboxylic acid ethyl ester

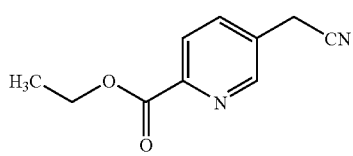

10.5 g (52.6 mmol) 5-(chloromethyl)pyridine-2-carboxylic acid ethyl ester

[preparation according to H. Barth et al., *Liebigs Ann. Chem.* 1981, 2164-2179] are initially introduced into 75 ml anhydrous DMF and 2.58 g (52.6 mmol) sodium cyanide are added in portions at RT in the course of 3 h. The mixture is then introduced on to 500 ml saturated ammonium chloride solution and extracted with methylene chloride (four times with 100 ml each time). The combined organic phases are dried over sodium sulfate and concentrated and the residue is purified by chromatography over silica gel (mobile phase: cyclohexane→cyclohexane/ethyl acetate 1:4). 3.80 g (38% of th.) of the title compound are obtained.

$^1$H-NMR (300 MHz, DMSO-$d_6$): δ=8.69 (d, 1H), 8.10 (d, 1H), 7.99 (dd, 1H), 4.36 (q, 2H), 4.24 (s, 2H), 1.34 (t, 3H).

LC-MS (Method 3): $R_t$=1.45 min; MS (ESIpos): m/z=191 [M+H]$^+$.

The compounds listed in Table 3 are obtained in an analogous manner to Example 10A from the corresponding educts:

TABLE 3

| Example no. | Structure | MS (ESI) [M + H]$^+$ | LC-MS $R_t$ [min] (method) | Yield (% of th.) |
|---|---|---|---|---|
| 21A | H$_3$C-pyridine-CH$_2$-C(O)-O-CH$_2$CH$_3$ | 180 | 2.16 (1) | 93 |
| 22A | H$_3$C-CH$_2$-O-C(O)-pyridine-CH$_2$-C(O)-O-CH$_2$CH$_3$ | 238 | 1.79 (3) | 82 |

Example 23A (4-Methylpyridin-3-yl)acetic acid ethyl ester

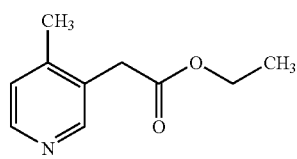

The synthesis of the title compound is carried out analogously to Example 13A from 200 mg (1.32 mmol) (4-methylpyridin-3-yl)acetic acid.

Yield: 235 mg (99% of th.)

$^1$H-NMR (300 MHz, DMSO-$d_6$): δ=8.32 (d, 1H), 7.56 (dd, 1H), 7.20. (dd, 1H), 4.08 (q, 2H), 3.67 (s, 2H), 2.44 (s, 3H), 1.18 (t, 3H).

LC-MS (Method 1): $R_t$=1.86 min; MS (ESIpos): m/z=180 [M+H]$^+$.

Example 24A (6-Methylpyridin-3-yl)acetic acid ethyl ester

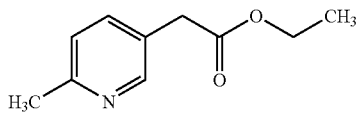

The synthesis of the title compound is carried out analogously to Example 13A from 493 mg (3.26 mmol) (6-methylpyridin-3-yl)acetic acid [preparation: N. Sperber et al., *J. Am. Chem. Soc.* 81, 704-709 (1959)].

Yield: 580 mg (99% of th.)

$^1$H-NMR (300 MHz, DMSO-$d_6$): δ=8.32 (d, 1H), 7.57 (dd, 1H), 7.20 (d, 1H), 4.08 (q, 2H), 3.67 (s, 2H), 2.44 (s, 3H), 1.18 (t, 3H).

LC-MS (Method 1): $R_t$=1.85 min; MS (ESIpos): m/z=180 [M+H]$^+$.

The compounds listed in Table 4 are prepared analogously to Example 14A from the corresponding educts:

TABLE 4

| Example no. | Structure | Yield (% of th.) | MS (ESI) [M + H]+; LC-MS R_t [min] (method) | 1H-NMR |
|---|---|---|---|---|
| 25A | (structure: ethyl 2-(5-methylpyridin-3-yl)-3-(dimethylamino)acrylate) | 84 | m/z = 235; 1.08 min (5) | (400 MHz, DMSO-d_6): δ = 8.21 (d, 1 H), 8.11 (d, 1 H), 7.57 (s, 1 H), 7.32 (s, 1 H), 4.00 (q, 2 H), 2.66 (s, 6 H), 2.28 (s, 3 H), 1.11 (t, 3 H). |
| 26A | (structure: ethyl 2-(6-methylpyridin-3-yl)-3-(dimethylamino)acrylate) | 50 | m/z = 235; 2.17 min (1) | |
| 27A | (structure: ethyl 2-(4-methylpyridin-3-yl)-3-(dimethylamino)acrylate) | 35 | m/z = 235; 2.21 min (1) | |
| 28A | (structure: diethyl 5-[3-(dimethylamino)-1-ethoxy-1-oxoprop-2-en-2-yl]pyridine-2-carboxylate) | 81 | m/z = 293; 2.02 min (5) | (300 MHz, DMSO-d_6): δ = 8.44 (d, 1 H), 7.96 (d, 1 H), 7.68 (s, 1 H), 7.66 (dd, 1 H), 4.33 (q, 2 H), 4.03 (q, 2 H), 2.71 (br. s, 6 H), 1.33 (t, 3 H), 1.13 (t, 3 H). |

The compounds listed in Table 5 are obtained analogously to Example 1A from the corresponding 2-chloropyridines. Instead of the working up described under Example 1A, the reaction solution is concentrated here and the residue is stirred with a mixture of diethyl ether and methylene chloride. The excess crystalline hydrazine hydrochloride is filtered off, the filtrate is concentrated and dried in vacuo and the product is reacted without further purification.

TABLE 5

| Example no. | Structure | MS (ESI) [M + H]+; LC-MS R_t [min] (method) | 1H-NMR (400 MHz, DMSO-d_6) |
|---|---|---|---|
| 29A | (structure: 5-bromo-2-hydrazinyl-4-methylpyridine) | m/z = 202; 2.14 min (1) | δ = 7.99 (s, 1 H), 7.52 (s, 1 H), 6.70 (s, 1 H), 4.14 (s, 2 H), 2.22 (s, 3 H). |

TABLE 5-continued

| Example no. | Structure | MS (ESI) [M + H]+; LC-MS $R_t$ [min] (method) | $^1$H-NMR (400 MHz, DMSO-$d_6$) |
|---|---|---|---|
| 30A | Cl-pyridine-NH-NH$_2$ | m/z = 144; 0.78 min (1) | δ = 7.96 (d, 1 H), 7.65 (s, 1 H), 7.50 (dd, 1 H), 6.73 (d, 1 H), 4.18 (s, 2 H). |
| 31A | Br-pyridine-NH-NH$_2$ | m/z = 188; 1.00 min (1) | |
| 32A | I-pyridine-NH-NH$_2$ | m/z = 236; 1.32 min (1) | δ = 8.11 (d, 1 H), 7.67 (dd, 1 H), 7.62 (s, 1 H), 6.60 (d, 1 H), 4.14 (s, 2 H). |

Example 33A

2-Hydrazino-isonicotinic acid nitrile

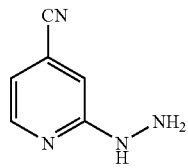

20.0 g (144 mmol) 2-chloroisonicotinic acid nitrile are initially introduced into 150 ml 1-butanol, 303 ml (303 mmol) of a 1 M solution of hydrazine hydrate in THF are added and the mixture is heated (110° C. bath temperature) for 16 h. The mixture is concentrated and the residue is purified by means of flash chromatography on silica gel (mobile phase: methylene chloride/methanol 10:1).

Yield: 9.48 g (49% of th.)

$^1$H-NMR (400 MHz, DMSO-$d_6$): δ=8.15 (d, 1H), 8.05 (s, 1H), 7.01 (s, 1H), 6.83 (dd, 1H), 4.30 (s, 2H).

LC-MS (Method 1): $R_t$=0.52 min; MS (ESIpos): m/z=135 [M+H]+.

Example 34A (6-Hydrazinopyridin-3-yl)methanol

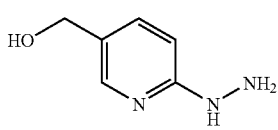

20.0 g (139 mmol) (6-chloropyridin-3-yl)methanol are heated under reflux overnight in 400 ml of a 35% strength aqueous hydrazine hydrate solution. The mixture is concentrated, toluene is added, the mixture is concentrated again and the residue is stirred with a mixture of methylene chloride, methanol and diethyl ether. The crystalline residue (hydrazine hydrochloride) is filtered off, the filtrate is concentrated and the residue is dried in vacuo.

Yield: 19.3 g (99% of th.)

$^1$H-NMR (400 MHz, DMSO-$d_6$): δ=7.91 (d, 1H), 7.40 (dd, 1H), 7.29 (s, 1H), 6.66 (d, 1H), 4.93 (s, 1H), 4.31 (s, 2H), 4.14 (s, 2H).

LC-MS (Method 1): $R_t$=0.50 min; MS (ESIpos): m/z=140 [M+H]+.

Example 35A

Benzophenone (4-methoxypyridin-2-yl)hydrazone

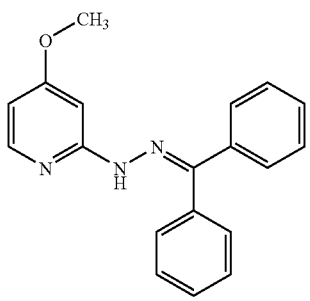

500 mg (3.48 mmol) 2-chloro-4-methoxypyridine, 752 mg (3.83 mmol) benzophenone hydrazone, 469 mg (4.88 mmol) sodium tert-butylate, 15.6 mg (0.07 mmol) palladium(II) acetate, 21.2 mg (0.17 mmol) phenylboronic acid and 43.4 mg (0.07 mmol) racemic 2,2'-bis(diphenylphosphino)-1,1'-binaphthyl are heated in degassed toluene at 90° C. overnight under argon. After cooling, the reaction mixture is poured into water, the aqueous phase is extracted several times with ethyl acetate and the combined organic phases are dried over sodium sulfate, filtered and concentrated. The residue is purified by means of preparative HPLC (RP18 column; mobile phase: acetonitrile/water gradient).

Yield: 872 mg (83% of th.)

$^1$H-NMR (400 MHz, DMSO-d$_6$): δ=10.8 (s, 1H), 8.07 (d, 1H), 7.70-7.64 (m, 5H), 7.50-7.38 (m, 5H), 6.94 (d, 1H), 6.78 (dd, 1H), 3.92 (s, 3H).

LC-MS (Method 3): R$_t$=1.70 min; MS (ESIpos): m/z=304 [M+H]$^+$.

Example 36A

2-Hydrazino-4-methoxypyridine

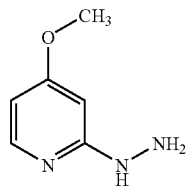

850 mg (2.80 mmol) of the compound from Example 35A are heated in concentrated hydrochloric acid overnight at 65° C. After cooling, the reaction mixture is washed with methylene chloride and concentrated. 470 mg of the crude product are obtained as the hydrochloride. 250 mg thereof are stirred with polymer-bonded tris(2-aminoethyl)amine in methylene chloride overnight at RT. The mixture is filtered, the filtrate is concentrated and the residue is dried under a high vacuum.

Yield: 170 mg (39% of th.)

$^1$H-NMR (400 MHz, DMSO-d$_6$): δ=7.78 (d, 1H), 7.26 (s, 1H), 6.25 (d, 1H), 6.15 (dd, 1H), 4.09 (s, 2H), 3.73 (s, 3H).

LC-MS (Method 1): R$_t$=0.89 min; MS (ESIpos): m/z=140 [M+H]$^+$.

Example 37A 3-(Chloromethyl)-2-methylpyridine

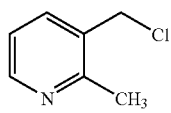

1.00 g (8.12 mmol) 3-(hydroxymethyl)-2-methylpyridine are initially introduced into the reaction vessel and 5.9 ml (81.2 mmol) thionyl chloride are slowly added at 0° C. The mixture is stirred under reflux for 3 h. It is concentrated, saturated sodium bicarbonate solution is added to the residue and the mixture is extracted several times with diethyl ether. The combined organic phases are washed with saturated sodium chloride solution, dried over sodium sulfate, filtered and concentrated.

Yield: 0.98 g (85% of th.)

GC-MS (Method 7): R$_t$=4.85 min; MS (EIpos): m/z=141 [M]$^+$.

Example 38A (2-Methylpyridin-3-yl)acetonitrile

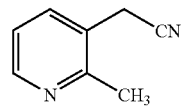

970 mg (6.85 mmol) of the compound from Example 37A are initially introduced into 10 ml DMF, 336 mg (6.85 mmol) sodium cyanide are added and the mixture is stirred overnight at 45° C. The reaction mixture is introduced on to 75 ml saturated ammonium chloride solution and extracted several times with methylene chloride. The combined organic phases are dried over sodium sulfate, filtered and concentrated. The residue is purified by means of flash chromatography on silica gel (mobile phase: methylene chloride/methanol 20:1).

Yield: 795 mg (88% of th.)

GC-MS (Method 7): R$_t$=6.14 min; MS (EIpos): m/z=132 [M]$^+$.

Example 39A (2-Methylpyridin-3-yl)acetic acid ethyl ester

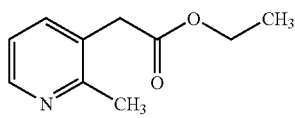

790 mg (5.98 mmol) of the compound from Example 38A are initially introduced into 10 ml ethanol, 4 ml concentrated sulfuric acid are added slowly and the mixture is heated under reflux for 6 h. After cooling, the mixture is neutralized with 6.00 g sodium bicarbonate and saturated sodium bicarbonate solution. The aqueous phase is extracted several times with ethyl acetate and the combined organic phases are dried over sodium sulfate, filtered and concentrated. The residue is reacted without further purification.

Yield: 614 mg (57% of th.)

$^1$H-NMR (400 MHz, DMSO-d$_6$): δ=8.34 (dd, 1H), 7.57 (dd, 1H), 7.18 (dd, 1H), 4.10 (q, 2H), 3.73 (s, 2H), 2.40 (s, 3H), 1.18 (t, 3H).

LC-MS (Method 1): R$_t$=1.84 min; MS (ESIpos): m/z=180 [M+H]$^+$.

Example 40A (6-Trifluoromethylpyridin-3-yl)-acetic acid ethyl ester

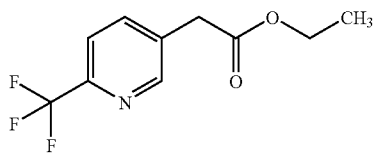

4.23 g (20.6 mmol) (6-trifluoromethylpyridin-3-yl)acetic acid [obtainable from [6-trifluoromethyl)pyridin-3-yl]methanol analogously to the reaction sequence of Examples 37A, 38A and 41] are initially introduced into 200 ml ethanol under argon, 0.2 ml concentrated sulfuric acid are added and the mixture is heated under reflux for 5 h. After cooling, the reaction solution is concentrated, the residue is taken up in ethyl acetate and the mixture is washed with saturated sodium bicarbonate solution. The aqueous phase is re-extracted several times with ethyl acetate and the combined organic phases are dried over sodium sulfate, filtered and concentrated. The residue is purified by means of flash chromatography on silica gel (mobile phase: gradient cyclohexane→cyclohexane/ethyl acetate 1:1).

Yield: 3.24 g (67% of th.)

$^1$H-NMR (400 MHz, DMSO-d$_6$): δ=8.69 (s, 1H), 8.02 (d, 1H), 7.89 (d, 1H), 4.13 (q, 2H), 3.91 (s, 2H), 1.21 (t, 3H).

LC-MS (Method 3): R$_t$=2.12 min; MS (ESIpos): m/z=234 [M+H]$^+$.

Example 41A

3-Hydroxy-2-(6-trifluoromethylpyridin-3-yl)-acrylic acid ethyl ester

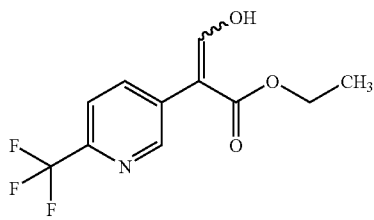

3.46 g (14.8 mmol) of the compound from Example 40A are initially introduced into 50 ml anhydrous toluene under argon, 712 mg (17.8 mmol) sodium hydride suspension (60% strength in paraffin oil) are added in portions and the mixture is stirred at RT for 1 h and then at 80° C. for 20 min. After cooling, 392 mg (1.48 mmol) 18-crown-6 and then, while cooling with ice, 2.20 g (29.7 mol) formic acid ethyl ester are added dropwise. The mixture is stirred first at 0° C. for 1 h and then at RT for 1 h. A mixture of 100 ml ethyl acetate and 150 ml 0.1 M hydrochloric acid is added, the phases are separated, the aqueous phase is extracted several times with ethyl acetate and the combined organic phases are dried over sodium sulfate, filtered and concentrated. The residue is purified by means of flash chromatography on silica gel (mobile phase: cyclohexane/ethyl acetate gradient).

Yield: 3.9 g (100% of th.)

$^1$H-NMR (400 MHz, DMSO-d$_6$): δ=11.8 (s, 1H), 8.70 (d, 1H), 8.03 (s, 1H), 8.00 (d, 1H), 7.87 (d, 1H), 4.15 (q, 2H), 1.21 (t, 3H).

Example 42A 3-(Dimethylamino)-2-pyridin-3-yl-acrylic acid ethyl ester

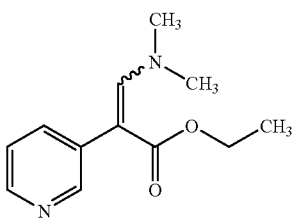

37.4 g (226 mmol) pyridin-3-ylacetic acid ethyl ester are heated in 100 g (679 mmol) dimethylformamide diethyl acetal overnight at 100° C. After cooling, the mixture is concentrated and the residue is pre-purified by means of flash chromatography on silica gel (mobile phase: gradient cyclohexane/ethyl acetate 1:1→ethyl acetate/ethanol 9:1). The product obtained is subjected to fine purification by vacuum distillation (1 mbar, 200° C. bath temperature).

Yield: 35.0 g (70% of th.)

$^1$H-NMR (400 MHz, DMSO-d$_6$): δ=8.37 (dd, 1H), 8.31 (dd, 1H), 7.59 (s, 1H), 7.51 (dt, 1H), 7.29 (ddd, 1H), 4.00 (q, 2H), 2.67 (s, 6H), 1.11 (t, 3H).

LC-MS (Method 1): R$_t$=2.38 min; MS (ESIpos): m/z=221 [M+H]$^+$.

Example 43A 3-(Dimethylamino)-2-(2-methylpyridin-3-yl)-acrylic acid ethyl ester

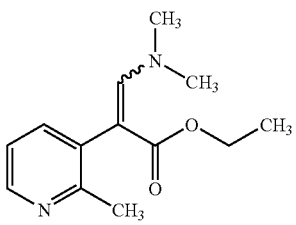

600 mg (3.35 mmol) of the compound from Example 39A are heated in 1.7 ml (10.0 mmol) dimethylformamide diethyl acetal overnight at 100° C. After cooling, the mixture is concentrated and the residue is purified by means of preparative HPLC (RP18 column; mobile phase: acetonitrile/water gradient).

Yield: 619 mg (79% of th.)

$^1$H-NMR (400 MHz, DMSO-d$_6$): δ=8.30 (dd, 1H), 7.54 (s, 1H), 7.38 (dd, 1H), 7.13 (dd, 1H), 4.05-3.92 (m, 2H), 2.62 (s, 6H), 2.30 (s, 3H), 1.08 (t, 3H).

LC-MS (Method 1): $R_t$=2.19 min; MS (ESIpos): m/z=235 [M+H]$^+$.

Embodiment Examples

Example 1

4-Pyridin-3-yl-2-pyrimidin-2-yl-1,2-dihydro-3H-pyrazol-3-one

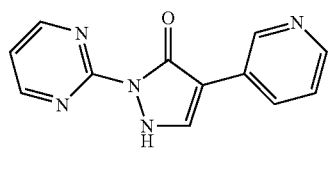

193 mg (1 mmol) of the compound from Example 2A and 116 mg (1.05 mmol) 2-hydrazinopyrimidine are initially introduced into 2 ml anhydrous ethanol under argon and the mixture is stirred at RT for 20 h. 40 mg (1 mmol) sodium hydride suspension (60% strength in paraffin oil) are then added in portions, a significant clouding of the reaction solution developing. The mixture is subsequently stirred at RT for 10 min. 1 ml 1 M hydrochloric acid is then added to the dark reaction mixture, a precipitate separating out. The precipitate is filtered off with suction and the residue is washed with water (2×1 ml) and dried in vacuo. 173 mg (72% of th.) of the title compound are obtained.

$^1$H-NMR (300 MHz, DMSO-d$_6$): δ=12.8 (br. s, 1H), 9.04 (d, 1H), 8.92 (d, 2H), 8.38 (m, 2H), 8.19 (d, 1H), 7.50 (dd, 1H), 7.42 (dd, 1H).

LC-MS (Method 5): $R_t$=0.59 min; MS (ESIpos): m/z=240 [M+H]$^+$.

Example 2

2-(4-Methylpyridin-2-yl)-4-pyridin-3-yl-1,2-dihydro-3H-pyrazol-3-one

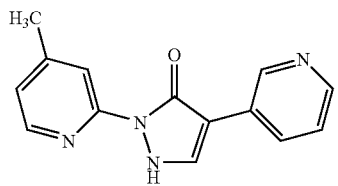

1.53 g (7.90 mmol) of the compound from Example 2A and 2.92 g (23.7 mmol) of the compound from Example 1A are dissolved 2 ml anhydrous ethanol under argon and the mixture is stirred at RT for 16 h. 537 g (7.90 mmol) sodium ethanolate are added, the reaction solution becoming dark red in color. The mixture is subsequently stirred at RT for 30 min and 7.9 ml 1 M hydrochloric acid are then added. The solution is partly concentrated, a precipitate separating out. This is filtered off, washed with water (twice with 5 ml each time) and with MTBE (5 ml) and dried in vacuo. 435 mg (22% of th.) of the title compound are obtained.

$^1$H-NMR (400 MHz, DMSO-d$_6$): δ=9.06 (d, 1H), 8.35 (m, 3H), 8.20 (d, 1H), 8.08 (s, 1H), 7.37 (dd, 1H), 7.21 (d, 1H), 2.45 (s, 3H).

LC-MS (Method 5): $R_t$=1.42 min; MS (ESIpos): m/z=253 [M+H]$^+$.

Example 3

4-Pyridin-3-yl-2-[5-(trifluoromethyl)pyridin-2-yl]-1,2-dihydro-3H-pyrazol-3-one

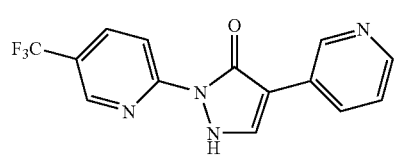

The compound is prepared analogously to Example 2 from 580 mg (3.00 mmol) of the compound from Example 2A and 558 mg (3.00 mmol) 2-hydrazino-5-(trifluoromethyl)pyridine.

Yield: 55 mg (6% of th.)

HPLC (Method 6): $R_t$=3.7 min.

MS (ESIpos): m/z=307 [M+H]$^+$ $^1$H-NMR (of the ethanol adduct) (300 MHz, DMSO-d$_6$): δ=13.3 (s, 1H), 9.14 (d, 1H), 8.86 (d, 1H), 8.66 (d, 1H), 8.60 (s, 1H), 8.31-8.41 (m, 3H), 7.40 (dd, 1H), 4.36 (s, 1H), 3.45 (q, 2H), 1.05 (t, 3H).

Example 4

2-(5-Oxo-4-pyridin-3-yl-2,5-dihydro-1H-pyrazol-1-yl)isonicotinic acid tert-butyl ester

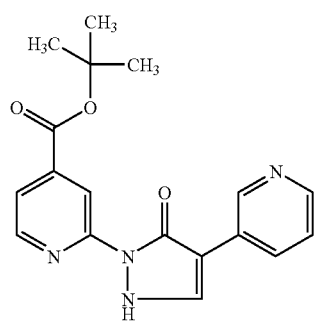

The compound is prepared analogously to Example 2 from 500 mg (2.59 mmol) of the compound from Example 2A and 662 mg (2.85 mmol) 2-hydrazino-5-isonicotinic acid tert-butyl ester. 288 mg (33% of th.) of the title compound are obtained as a yellow solid.

$^1$H-NMR (300 MHz, CDCl$_3$): δ=12.7 (br. s, 1H), 8.97 (d, 1H), 8.47-8.41 (m, 3H), 8.03 (dt, 1H), 7.91 (s, 1H), 7.76 (dd, 1H), 7.32 (dd, 1H), 1.64 (s, 9H).

LC-MS (Method 5): $R_t$=1.75 min; MS (ESIpos): m/z=339 [M+H]$^+$.

Example 5

4-Pyridin-3-yl-2-[4-(trifluoromethyl)pyridin-2-yl]-1,2-dihydro-3H-pyrazol-3-one

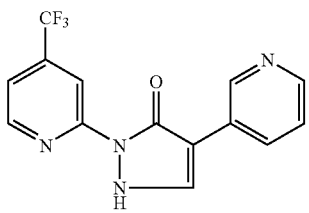

The compound is prepared analogously to Example 2 from 18 mg (0.09 mmol) of the compound from Example 2A and 18 mg (0.10 mmol) 2-hydrazino-4-(trifluoromethyl)pyridine [R. A. Evans, C. Wentrup, *J. Chem. Soc. Chem. Commun.* 15, 1062-1064 (1992)]. 11.7 mg (41% of th.) of the title compound are obtained as a yellow solid.

$^1$H-NMR (400 MHz, CDCl$_3$): δ=12.6 (br. s, 1H), 8.97 (s, 1H), 8.53 (d, 1H), 8.46 (d, 1H), 8.25 (s, 1H), 8.01 (d, 1H), 7.92 (s, 1H), 7.45 (d, 1H), 7.32 (dd, 1H).

LC-MS (Method 5): $R_t$=1.50 min; MS (ESIpos): m/z=307 [M+H]$^+$.

Example 6

2-Pyridin-2-yl-4-pyridin-3-yl-1,2-dihydro-3H-pyrazol-3-one

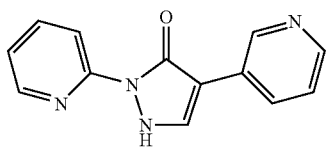

3.95 g (13.9 mmol) of the compound from Example 3A are initially introduced into 80 ml ethanol under argon and 945 mg (13.9 mmol) sodium ethanolate are added in portions at RT. After stirring for 30 min, 13.9 ml 1 M hydrochloric acid are added dropwise. The precipitate which has separated out is filtered off with suction, washed with cold ethanol (20 ml) and with water (twice with 20 ml each time) and dried in vacuo. 2.80 g (85% of th.) of the title compound are obtained.

$^1$H-NMR (400 MHz, CDCl$_3$): δ=13.5 (br. s, 1H), 8.97 (d, 1H), 8.44 (dd, 1H), 8.34 (d, 1H), 8.05-7.91 (m, 3H), 7.87 (s, 1H), 7.31 (dd, 1H), 7.25 (m, 1H).

HPLC (Method 6): $R_t$=3.00 min.

MS (DCI): m/z=239 [M+H]$^+$.

Example 7

4-(6-Chloropyridin-3-yl)-2-pyridin-2-yl-1,2-dihydro-3H-pyrazol-3-one 5.06 g (19.9 mmol) of the compound from Example 16A and 4.34 g (39.7 mmol) 2-hydrazinopyridine are stirred in 100 ml glacial acetic acid at RT for 2 h. The mixture is concentrated, the residue is taken up in 300 ml ethyl acetate and the mixture is washed with saturated sodium bicarbonate solution (twice with 100 ml each time). The organic phase is dried over sodium sulfate, filtered and concentrated. The residue obtained is taken up in 100 ml ethanol, 1.49 g (21.9 mmol) sodium ethanolate are added in portions, while cooling in an ice bath, and the mixture is subsequently stirred at 0° C. for 30 min. 22 ml 1 M hydrochloric acid are added to the reaction solution at 0° C. and the mixture is stirred at this temperature for a further 30 min. The precipitate formed is filtered off with suction and washed with cold ethanol. After drying in vacuo, 3.18 g (59% of th.) of the title compound are obtained.

$^1$H-NMR (300 MHz, DMSO-d$_6$): δ=8.93 (s, 1H), 8.50 (d, 2H), 8.34 (d, 2H), 8.05 (dd, 1H), 7.51 (d, 1H), 7.36 (dd, 1H).

LC-MS (Method 3): $R_t$=2.27 min; MS (ESIpos): m/z=273 [M+H]$^+$.

The examples listed in Table 6 are obtained analogously to Example 7 from the corresponding educts:

TABLE 6

| Example no. | Structure | MS (ESI) [M + H]$^+$ | LC-MS $R_t$ [min] (method) | Yield (% of th.) |
|---|---|---|---|---|
| 8 | 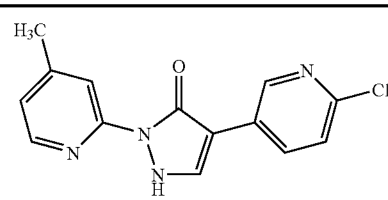 | 287 | 2.37 (3) | 49 |
| 9 | 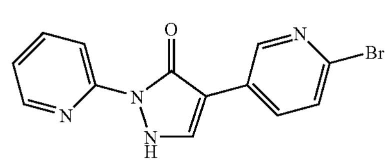 | 317 | 2.32 (3) | 63 |

TABLE 6-continued

| Example no. | Structure | MS (ESI) [M + H]+ | LC-MS Rt [min] (method) | Yield (% of th.) |
|---|---|---|---|---|
| 10 | 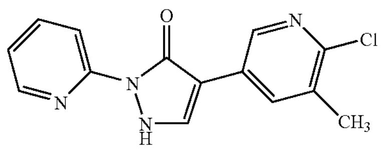 | 287 | 2.38 (3) | 97 |

Example 11

5-[2-(4-Methylpyridin-2-yl)-3-oxo-2,3-dihydro-1H-pyrazol-4-yl]pyridine-2-carbonitrile

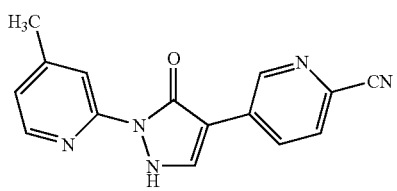

100 mg (0.35 mmol) of the compound from Example 8, 8.19 mg (0.70 mmol) zinc cyanide and 40.3 mg (0.03 mmol) tetrakis(triphenylphosphine)palladium(0) are initially introduced into 4 ml anhydrous DMF under argon and the reaction mixture is stirred at 190° C. for 90 min under microwave irradiation (single mode apparatus Explorer from CEM). The reaction mixture is filtered off with suction over kieselguhr, the residue is rinsed with DMF and the filtrate is concentrated on a rotary evaporator. The residue obtained in this way is chromatographed via preparative HPLC (column: YMC GEL ODS-AQ S-5/15 µm; gradient: acetonitrile/water+0.2% TFA 10:90→95:5). The solid obtained from the combined product fractions is washed with 6 ml methylene chloride, filtered off with suction and dried in vacuo.

Yield: 7 mg (7% of th.)

$^1$H-NMR (400 MHz, DMSO-d$_6$): δ=9.23 (d, 1H), 8.55 (s, 1H), 8.43 (dd, 1H), 8.35 (d, 1H), 8.15 (s, 1H), 7.94 (d, 1H), 7.25 (d, 1H), 2.47 (s, 3H).

LC-MS (Method 3): R$_t$=2.01 min; MS (ESIpos): m/z=278 [M+H]+.

Example 12

5-(3-Oxo-2-pyridin-2-yl-2,3-dihydro-1H-pyrazol-4-yl)pyridine-2-carbonitrile

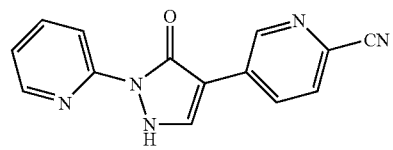

The preparation is carried out analogously to Example 11 from 100 mg (0.37 mmol) of the compound from Example 7.

Yield: 12 mg (12% of th.)

$^1$H-NMR (400 MHz, DMSO-d$_6$): δ=9.27 (s, 1H), 8.66 (s, 1H), 8.50 (m, 2H), 8.35 (d, 1H), 8.08 (dd, 1H), 7.97 (d, 1H), 7.38 (dd, 1H).

LC-MS (Method 3): R$_t$=1.70 min; MS (ESIpos): m/z=264 [M+H]+.

Example 13

4-(5-Bromopyridin-3-yl)-2-pyridin-2-yl-1,2-dihydro-3H-pyrazol-3-one

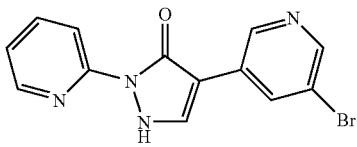

The synthesis of the title compound is carried out analogously to Example 7 from 1.40 g (3.50 mmol) of the compound from Example 17A.

Yield: 345 mg (31% of th.)

LC-MS (Method 5): R$_t$=2.24 min; MS (ESIpos): m/z=319 [M+H]+.

Example 14

5-(3-Oxo-2-pyridin-2-yl-2,3-dihydro-1H-pyrazol-4-yl)nicotinonitrile

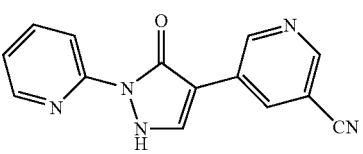

The preparation is carried out analogously to Example 11 from 50 mg (0.16 mmol) of the compound from Example 13.

Yield: 20 mg (48% of th.)

$^1$H-NMR (300 MHz, DMSO-d$_6$): δ=9.40 (d, 1H), 8.76 (d, 1H), 8.72 (m, 1H), 8.61 (s, 1H), 8.51 (d, 1H), 8.36 (d, 1H), 8.07 (dd, 1H), 7.37 (dd, 1H).

LC-MS (Method 3): $R_t$=1.65 min; MS (ESIpos): m/z=264 [M+H]$^+$.

Example 15

5-Methyl-2-pyridin-2-yl-4-pyridin-3-yl-1,2-dihydro-3H-pyrazol-3-one

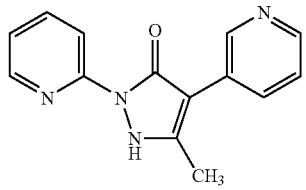

22 μl glacial acetic acid are added to a solution of 58 mg (0.28 mmol) of the compound from Example 18A and 34 mg (0.31 mmol) 2-hydrazinopyridine in 0.4 ml absolute ethanol and the mixture is stirred overnight at RT. 19 mg sodium ethylate are added and the mixture is subsequently stirred at RT for 30 min and then neutralized with 1 N hydrochloric acid. After addition of water, the mixture is extracted with methylene chloride and the organic phase is dried over magnesium sulfate, filtered and concentrated. The residue is stirred with diisopropyl ether and the solid is filtered off with suction. After drying, 13.5 mg (19% of th.) of the title compound are obtained.

$^1$H-NMR (400 MHz, CDCl$_3$): δ=13.28 (br. s, 1H), 8.83 (s, 1H), 8.47 (d, 1H), 8.30 (d, 1H), 7.95-7.86 (m, 3H), 7.33 (dd, 1H), 7.18 (t, 1H), 2.44 (s, 3H).

LC-MS (Method 1): $R_t$=2.11 min; MS (ESIpos): m/z=253 [M+H]$^+$.

Example 16

4-(6-Hydroxypyridin-3-yl)-2-pyridin-2-yl-1,2-dihydro-3H-pyrazol-3-one

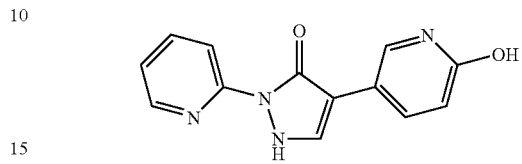

50.0 mg (0.18 mmol) of the compound from Example 7 and 600 mg (7.74 mmol) ammonium acetate are heated at 180° C. as a suspension in 3 ml glacial acetic acid in a single mode microwave (Explorer from CEM) for 2 h. After a complete conversion is detected by analytical HPLC, toluene is added and the volatile components are distilled off azeotropically. The residue is taken up in water and the solid which remains is filtered off. The slightly brownish powder is subsequently washed with water and then with MTBE. After drying, 39 mg (84% of th.) of the title compound are obtained.

$^1$H-NMR (300 MHz, DMSO-d$_6$): δ=12.7 (br. s, 1H), 11.58 (br. s, 1H), 8.47 (d, 1H), 8.32 (m, 1H), 8.21 (s, 1H), 8.01 (m, 2H), 7.87 (dd, 1H), 7.32 (dd, 1H), 6.39 (d, 1H).

LC-MS (Method 3): $R_t$=1.31 min; MS (ESIpos): m/z=255 [M+H]$^+$.

The examples listed in Table 7 are prepared analogously to Example 7 from the corresponding educts:

TABLE 7

| Example no. | Structure | MS (ESI) [M + H]$^+$ | LC-MS $R_t$ [min] (method) | Yield (% of th.) |
|---|---|---|---|---|
| 17 | 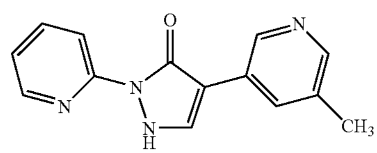 | 253 | 1.06 (5) | 9* |
| 18 | 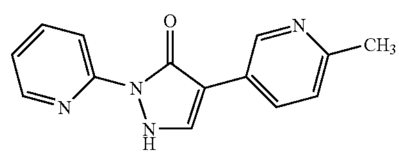 | 253 | 2.20 (1) | 13* |
| 19 | 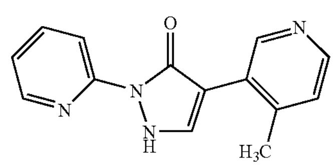 | 253 | 1.01 (5) | 30* |
| 20 | 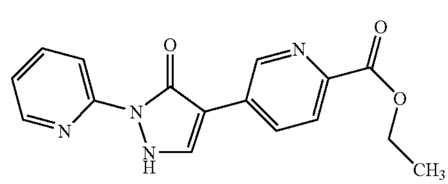 | 311 | 1.90 (3) | 31 |

[*Purification of the crude product via preparative HPLC (column: YMC Gel ODS-AQ S-5/15 μm; gradient: acetonitrile/water + 0.2% trifluoroacetic acid 10:90 → 95:5)].

Example 21

4-[6-(Hydroxymethyl)pyridin-3-yl]-2-pyridin-2-yl-1,2-dihydro-3H-pyrazol-3-one

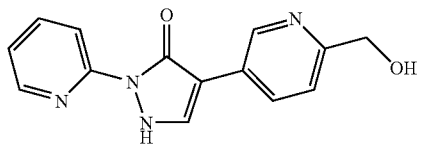

73 mg (1.93 mmol) sodium borohydride are initially introduced into 20 ml ethanol and 115 mg (1.03 mmol) calcium chloride are added at 0° C. The compound from Example 20 (400 mg, 1.29 mmol) is added in portions and the mixture is stirred at 0° C. for 1 h and thereafter at RT for 4 h. To bring the reaction to completion, a further 73 mg (1.93 mmol) sodium borohydride are added and the mixture is stirred at RT for 20 h. Hydrolysis is carried out with 5 ml water and the mixture is rendered weakly acid with 1 N hydrochloric acid. The mixture is then stirred at RT for 1 h. It is concentrated and the residue is taken up in approx. 16 ml DMSO/water mixture (1:1) and purified in portions via preparative HPLC (column: YMC Gel ODS-AQ S-5/15 μm; gradient: acetonitrile/water+ 0.2% trifluoroacetic acid 10:90→95:5).

Yield: 332 mg (96% of th.)

$^1$H-NMR (400 MHz, DMSO-$d_6$): δ=9.19 (s, 1H), 8.71 (d, 1H), 8.64 (s, 1H), 8.51 (d, 1H), 8.37 (d, 1H), 8.09 (dd, 1H), 7.81 (d, 1H), 7.38 (dd, 1H), 4.77 (s, 2H).

LC-MS (Method 3): $R_t$=0.65 min; MS (ESIpos): m/z=269 [M+H]$^+$.

Example 22

2-Pyridin-2-yl-4-(6-trifluormethylpyridin-3-yl)-1,2-dihydro-3H-pyrazol-3-one

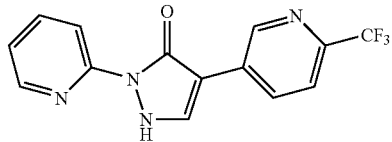

261 mg (1.00 mmol) of the compound from Example 41A and 115 mg (1.05 mmol) 2-hydrazinopyridine are dissolved in 5 ml anhydrous ethanol under argon and the mixture is stirred at RT for 20 h. 68 mg (1.00 mmol) sodium ethanolate are added, the mixture is stirred at RT for 30 min and 1 M hydrochloric acid and a little ethanol are then added, a precipitate separating out. This is filtered off, washed with a little ethanol and dried in vacuo.

Yield: 180 mg (59% of th.)

$^1$H-NMR (400 MHz, DMSO-$d_6$): δ=9.26 (s, 1H), 8.63 (s, 1H), 8.55 (d, 1H), 8.51 (d, 1H), 8.35 (d, 1H), 8.05 (t, 1H), 7.87 (d, 1H), 7.37 (dd, 1H).

LC-MS (Method 4): $R_t$=2.15 min; MS (ESIpos): m/z=307 [M+H]$^+$.

Example 23

2-(5-Hydroxymethyl-pyridin-2-yl)-4-pyridin-3-yl-1,2-dihydro-3H-pyrazol-3-one hydrochloride

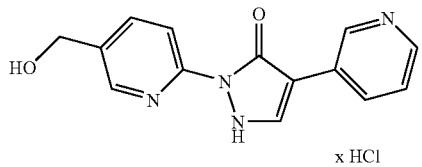

4.00 g (18.2 mmol) of the compound from Example 42A, 2.70 g (19.4 mmol) of the compound from Example 34A and 450 mg (1.94 mmol) camphor-10-sulfonic acid are dissolved in 120 ml anhydrous ethanol and the mixture is heated under reflux overnight. After cooling, the precipitate formed is filtered off with suction, washed with ethanol and diethyl ether and suspended in methanol, an excess of a 4 N solution of hydrogen chloride in 1,4-dioxane is added and the mixture is concentrated again. The residue is stirred with a mixture of methanol and methylene chloride, filtered off with suction and dried.

Yield: 3.23 g (66% of th.)

$^1$H-NMR (400 MHz, DMSO-$d_6$): δ=9.36 (s, 1H), 8.91 (d, 1H), 8.72 (s, 1H), 8.61 (d, 1H), 8.45-8.43 (m, 1H), 8.36 (d, 1H), 8.04 (dd, 1H), 7.98 (dd, 1H), 4.58 (s, 2H).

LC-MS (Method 1): $R_t$=2.12 min; MS (ESIpos): m/z=269 [M+H]$^+$.

The compounds listed in Table 8 are prepared from the corresponding educts analogously to Example 23. The purification of the particular precipitate can alternatively be carried out by means of preparative HPLC (RP18 column; mobile phase: acetonitrile/water gradient, with or without addition of 0.1% conc. hydrochloric acid).

TABLE 8

| Example no. | Structure | Educts; yield (% of th.) | MS (ESI) [M + H]$^+$; LC-MS $R_t$ [min] (method) | $^1$H-NMR (400 MHz, DMSO-$d_6$) |
|---|---|---|---|---|
| 24 | H$_3$C-pyridine-pyrazolone-pyridine-Br structure x HCl | 1A, 14A; 46% | m/z = 331; 2.24 min (4) | δ = 8.89 (d, 1 H), 8.45 (s, 1 H), 8.35 (d, 1 H), 8.20 (dd, 1 H), 8.11 (s, 1 H), 7.62 (d, 1 H), 7.22 (d, 1 H), 2.44 (s, 3 H). |

TABLE 8-continued

| Example no. | Structure | Educts; yield (% of th.) | MS (ESI) [M + H]+; LC-MS $R_t$ [min] (method) | 1H-NMR (400 MHz, DMSO-$d_6$) |
|---|---|---|---|---|
| 25 | 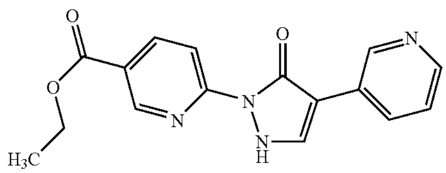 | 42A*; 25% | m/z = 311; 1.42 min (3) | δ = 9.13 (s, 1 H), 8.98 (s, 1 H), 8.62-8.52 (m, 2 H), 8.50-8.45 (m, 1 H), 8.37 (d, 1 H), 8.32 (d, 1 H), 7.41 (dd, 1 H), 4.37 (q, 2 H), 1.35 (t, 3 H). |
| 26 | 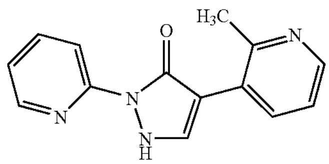 | 43A; 31% | m/z = 253; 2.16 min (1) | δ = 8.46 (d, 1 H), 8.34-8.28 (m, 2 H), 8.00 (dd, 1 H), 7.75-7.69 (m, 1 H), 7.52 (s, 1 H), 7.06-6.96 (m, 2 H), 2.56 (s, 3 H). |
| 27 | 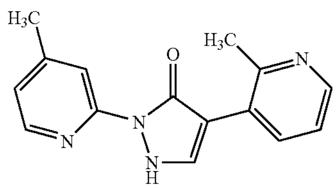 | 1A, 43A; 17% | m/z = 267; 1.13 min (5) | δ = 8.31-8.27 (m, 2 H), 8.19 (d, 1 H), 8.01 (dd, 1 H), 7.52 (s, 1 H), 7.04 (dd, 1 H), 6.86 (d, 1 H), 2.55 (s, 3 H), 2.32 (s, 3 H). |
| 28 | 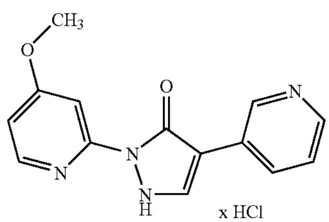 | 36A, 42A; 17% | m/z = 269; 1.25 min (5) | δ = 9.30 (d, 1 H), 8.89 (d, 1 H), 8.52 (s, 1 H), 8.50 (d, 1 H), 8.32 (d, 1 H), 7.96 (dd, 1 H), 7.85 (d, 1 H), 7.06 (dd, 1 H), 4.03 (s, 3 H). |

[*6-Hydrazinonicotinic acid ethyl ester can be obtained by esterification of 6-hydrazinonicotinic acid in ethanol analogously to Example 42].

Example 29

2-(4-Cyanopyridin-2-yl)-4-pyridin-3-yl-1,2-dihydro-3H-pyrazol-3-one

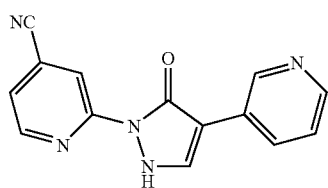

545 mg (4.06 mmol) of the compound from Example 33A and 1.07 g (4.88 mmol) of the compound from Example 42A are stirred in 15 ml glacial acetic acid at RT for 2 h. The mixture is concentrated, the residue is taken up in 300 ml ethyl acetate and the mixture is washed several times with saturated sodium bicarbonate solution. The organic phase is dried over sodium sulfate, filtered and concentrated. The residue is taken up in 30 ml ethanol, 1.33 g (4.88 mmol) of a 25% strength solution of sodium ethanolate in ethanol are added and the mixture is stirred for 30 min. A pH of 5 is established by addition of 1 M hydrochloric acid and the solid formed is filtered off with suction, washed with diethyl ether and dried under a high vacuum.

Yield: 890 mg (83% of th.)

1H-NMR (400 MHz, DMSO-$d_6$): δ=9.01-8.98 (m, 2H), 8.54 (dd, 1H), 8.18 (dt, 1H), 8.01 (dd, 1H), 7.85 (s, 1H), 7.39 (dd, 1H), 7.14 (dd, 1H).

LC-MS (Method 5): $R_t$=1.13 min; MS (ESIpos): m/z=264 [M+H]+.

Example 30

2-(5-Chloropyridin-2-yl)-4-pyridin-3-yl-1,2-dihydro-3H-pyrazol-3-one

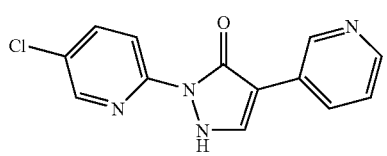

250 mg (1.74 mmol) of the compound from Example 30A and 460 mg (2.09 mmol) of the compound from Example 42A are stirred in 4 ml glacial acetic acid at RT for 0.5 h. The

Example 31

2-(5-Iodopyridin-2-yl)-4-pyridin-3-yl-1,2-dihydro-3H-pyrazol-3-one

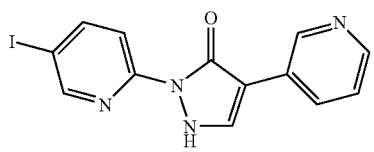

The synthesis of the title compound is carried out analogously to Example 30 from 250 mg (1.06 mmol) of the compound from Example 32A and 281 mg (1.28 mmol) of the compound from Example 42A.

Yield: 80 mg (21% of th.)

$^1$H-NMR (400 MHz, DMSO-d$_6$): δ=9.12 (s, 1H), 8.70 (s, 1H), 8.54-8.46 (m, 1H), 8.40-8.25 (m, 4H), 7.43-7.36 (m, 1H).

LC-MS (Method 3): R$_t$=1.44 min; MS (ESIpos): m/z=365 [M+H]$^+$.

Example 32

2-(5-Bromopyridin-2-yl)-4-pyridin-3-yl-1,2-dihydro-3H-pyrazol-3-one

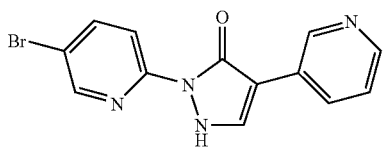

The synthesis of the title compound is carried out analogously to Example 30 from 250 mg (1.33 mmol) of the compound from Example 31A and 351 mg (1.60 mmol) of the compound from Example 42A.

Yield: 166 mg (39% of th.)

$^1$H-NMR (400 MHz, DMSO-d$_6$): δ=9.06 (d, 1H), 8.50 (d, 1H), 8.46 (s, 1H), 8.24 (d, 1H), 8.16 (d, 1H), 8.13 (s, 1H), 8.08 (dd, 1H), 7.24 (dd, 1H).

LC-MS (Method 5): R$_t$=1.40 min; MS (ESIpos): m/z=318 [M+H]$^+$.

Example 33

2-(5-Bromo-4-methylpyridin-2-yl)-4-pyridin-3-yl-1,2-dihydro-3H-pyrazol-3-one

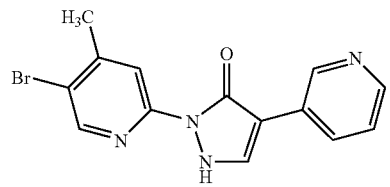

300 mg (1.49 mmol) of the compound from Example 29A and 392 mg (1.78 mmol) of the compound from Example 42A are stirred in 7 ml glacial acetic acid at RT for 36 h. The mixture is concentrated, the residue is taken up in ethyl acetate and the mixture is washed several times with saturated sodium bicarbonate solution. The organic phase is dried over magnesium sulfate, filtered and concentrated. The residue is taken up in 13 ml ethanol, 566 mg (2.08 mmol) of a 25% strength solution of sodium ethanolate in ethanol are added at RT and the mixture is stirred for 1 h. A pH of 5 is established by addition of 1 M hydrochloric acid, the mixture is concentrated and the residue is purified by means of preparative HPLC (RP18 column; mobile phase: acetonitrile/water gradient with addition of 0.1% conc. hydrochloric acid).

Yield: 55 mg (11% of th.)

$^1$H-NMR (400 MHz, DMSO-d$_6$): δ=9.41 (s, 1H), 8.99 (d, 1H), 8.86 (s, 1H), 8.67 (d, 1H), 8.60 (s, 1H), 8.45 (s, 1H), 8.03 (dd, 1H), 2.47 (s, 3H).

LC-MS (Method 3): R$_t$=1.53 min; MS (ESIpos): m/z=331 [M+H]$^+$.

Example 34

4-(6-Cyanopyridin-3-yl)-2-(4-methylpyridin-2-yl)-1,2-dihydro-3H-pyrazol-3-one hydrochloride

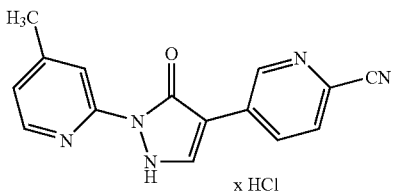

50 mg (136 μmol) of the compound from Example 24 are dissolved in 0.6 ml 1-methyl-2-pyrrolidone, 31.9 mg (272 μmol) zinc cyanide and 15.7 mg (14 μmol) tetrakis(triphenylphosphine)palladium(0) are added and the mixture is heated in a microwave at 200° C. for 30 min. The reaction mixture is filtered over kieselguhr and eluted with methanol. The filtrate is adjusted to a slightly acid pH by addition of 1 M hydrochloric acid and the precipitate is filtered off and purified by means of preparative HPLC (RP18 column; mobile phase: acetonitrile/water gradient with addition of 0.1% conc. hydrochloric acid).

Yield: 13 mg (31% of th.)

¹H-NMR (400 MHz, DMSO-d₆): δ=9.25 (s, 1H), 8.57 (s, 1H), 8.44 (d, 1H), 8.36 (d, 1H), 8.15 (s, 1H), 7.95 (d, 1H), 7.25 (d, 1H), 2.47 (s, 3H).

LC-MS (Method 4): R_t=2.20 min; MS (ESIpos): m/z=278 [M+H]⁺.

Example 35

2-[4-(Aminomethyl)pyridin-2-yl]-4-pyridin-3-yl-1,2-dihydro-3H-pyrazol-3-one dihydrochloride

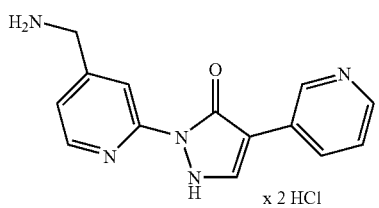

100 mg (380 μmol) of the compound from Example 29 are dissolved in 10 ml glacial acetic acid, 50.0 mg catalyst (10% palladium on charcoal) are added and the mixture is stirred overnight under a hydrogen atmosphere under normal pressure at RT. The reaction mixture is then filtered and concentrated and the residue is purified by means of preparative HPLC (RP18 column; mobile phase: acetonitrile/water gradient with addition of 0.1% conc. hydrochloric acid).

Yield: 64 mg (49% of th.)

¹H-NMR (400 MHz, DMSO-d₆): δ=9.38 (s, 1H), 8.93 (d, 1H), 8.79 (s, 1H), 8.75 (s, 3H), 8.64 (d, 1H), 8.56 (d, 1H), 8.48 (s, 1H), 7.99 (dd, 1H), 7.54 (d, 1H), 4.21 (q, 2H).

LC-MS (Method 1): R_t=1.39 min; MS (ESIpos): m/z=268 [M+H]⁺.

Example 36

N-{[2-(5-Oxo-4-pyridin-3-yl-2,5-dihydro-1H-pyrazol-1-yl)pyridin-4-yl]methyl}butanamide hydrochloride

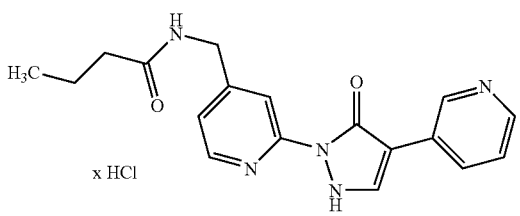

80.0 mg (235 μmol) of the compound from Example 35 and 22.8 mg (259 μmol) butyric acid are dissolved in 5 ml DMF, 119 mg (1.18 mmol) triethylamine and 90.2 mg (470 μmol) 1-(3-dimethylaminopropyl)-3-ethylcarbodiimide hydrochloride are added, while cooling with ice, and the mixture is stirred overnight at RT. The reaction mixture is then purified directly by means of preparative HPLC (RP18 column; mobile phase: acetonitrile/water gradient with addition of 0.1% conc. hydrochloric acid).

Yield: 7 mg (7% of th.)

¹H-NMR (400 MHz, DMSO-d₆): δ=9.33-9.31 (m, 1H), 8.87 (d, 1H), 8.66 (s, 1H), 8.61-8.56 (m, 2H), 8.43 (d, 1H), 8.25 (s, 1H), 7.96 (dd, 1H), 7.26 (d, 1H), 4.41 (d, 1H), 2.19 (t, 2H), 1.58 (sext, 2H), 0.90 (t, 3H).

LC-MS (Method 1): R_t=2.26 min; MS (ESIpos): m/z=338 [M+H]⁺.

Example 37

N-Isopropyl-N'-{[2-(5-oxo-4-pyridin-3-yl-2,5-dihydro-1H-pyrazol-1-yl)pyridin-4-yl]methyl}urea hydrochloride

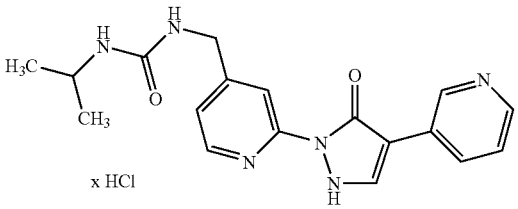

40.0 mg (470 μmol) isopropyl isocyanate are dissolved in 5 ml DMF under argon, 80.0 mg (235 μmol) of the compound from Example 35 and 71.4 mg (705 μmol) triethylamine are added and the mixture is stirred overnight at RT. The mixture is then concentrated and the residue is purified by means of preparative HPLC (RP18 column; mobile phase: acetonitrile/water gradient with addition of 0.1% conc. hydrochloric acid).

Yield: 80 mg (85% of th.)

¹H-NMR (400 MHz, DMSO-d₆): δ=9.35 (s, 1H), 8.95 (d, 1H), 8.66 (s, 1H), 8.59 (d, 1H), 8.42 (d, 1H), 8.24 (s, 1H), 8.02 (dd, 1H), 7.27 (d, 1H), 6.55 (s, 1H), 4.35 (s, 2H), 3.76-3.63 (m, 1H), 2.75 (s, 1H), 1.08-1.03 (m, 6H).

LC-MS (Method 1): R_t=2.81 min; MS (ESIpos): m/z=353 [M+H]⁺.

Example 38

N-{[2-(5-Oxo-4-pyridin-3-yl-2,5-dihydro-1H-pyrazol-1-yl)pyridin-4-yl]methyl}methanesulfonamide hydrochloride

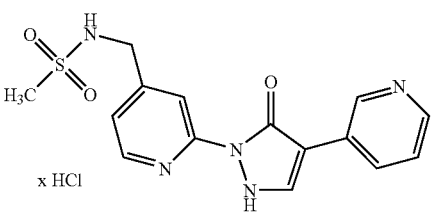

80.0 mg (235 μmol) of the compound from Example 35 and 53.9 mg (470 μmol) methanesulfonic acid chloride are dissolved in 5 ml DMF under argon and while cooling with ice, 152 mg (1.18 mmol) N,N-diisopropylethylamine are added and the mixture is stirred overnight at RT. The reaction mixture is then purified directly by means of preparative HPLC (RP18 column; mobile phase: acetonitrile/water gradient with addition of 0.1% conc. hydrochloric acid).

Yield: 31 mg (34% of th.)

¹H-NMR (400 MHz, DMSO-d₆): δ=9.34 (s, 1H), 8.88 (d, 1H), 8.69 (s, 1H), 8.59 (d, 1H), 8.47 (d, 1H), 8.40 (s, 1H), 7.95 (dd, 1H), 7.89 (t, 1H), 7.36 (d, 1H), 4.36 (d, 2H), 2.99 (s, 3H).

Example 39

6-(5-Oxo-4-pyridin-3-yl-2,5-dihydro-1H-pyrazol-1-yl)-nicotinic acid

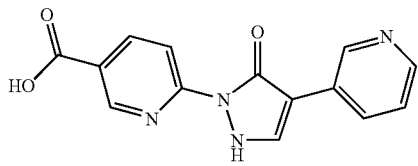

1.49 g (4.81 mmol) of the compound from Example 25 are dissolved 60 ml 1,4-dioxane, 40 ml of a 1 M aqueous lithium hydroxide solution are added and the mixture is heated under reflux for 1 h. The reaction mixture is then cooled to 0° C., adjusted to a weakly acid pH with 40 ml 1 M hydrochloric acid and stirred at 0° C. for 2 h. The precipitate formed is filtered off with suction, washed with water and diethyl ether and dried under a high vacuum.

Yield: 1.20 g (88% of th.)

$^1$H-NMR (400 MHz, DMSO-d$_6$): δ=9.40 (s, 1H), 9.00-8.94 (m, 2H), 8.90 (s, 1H), 8.66 (d, 1H), 8.60-8.54 (m, 1H), 8.49 (dd, 1H), 8.02 (dd, 1H).

LC-MS (Method 3): R$_t$=0.63 min; MS (ESIpos): m/z=283 [M+H]$^+$.

Example 40

N-Benzyl-6-(5-oxo-4-pyridin-3-yl-2,5-dihydro-1H-pyrazol-1-yl)-nicotinamide hydrochloride

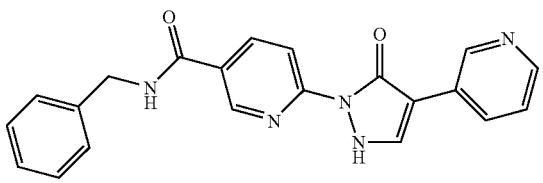

x HCl 50 mg (177 μmol) of the compound from Example 39 are dissolved in 2 ml DMF, 1.9 mg (16 μmol) 4-N,N-dimethylaminopyridine, 71.0 mg (549 μmol) N,N-diisopropylethylamine and 98.0 mg (188 μmol) benzotriazol-1-yloxy)-tripyrrolidinophosphonium hexafluorophosphate are added and the mixture is stirred at RT for 15 min. 25.2 mg (235 μmol) benzylamine are added and the mixture is stirred at RT for a further 5 h. To bring the conversion to completion, a further 25 mg (235 μmol) benzylamine are added and the mixture is stirred overnight at RT. The reaction mixture is pre-purified by means of preparative HPLC (RP18 column; mobile phase: acetonitrile/water gradient with addition of 0.1% conc. hydrochloric acid) and subsequent flash chromatography over silica gel (mobile phase: methylene chloride/methanol gradient), the crude product is precipitated from methanol and the precipitate is purified again by means of preparative HPLC (RP18 column; mobile phase: acetonitrile/water gradient with addition of 0.1% conc. hydrochloric acid).

Yield: 21 mg (30% of th.)

$^1$H-NMR (400 MHz, DMSO-d$_6$): δ=9.41 (s, 1H), 9.38-9.33 (m, 1H), 9.01 (s, 1H), 8.95 (d, 1H), 8.87 (s, 1H), 8.64 (d, 1H), 8.56-8.49 (m, 2H), 7.99 (dd, 1H), 7.38-7.32 (m, 4H), 7.30-7.24 (m, 1H), 4.53 (d, 2H).

LC-MS (Method 5): R$_t$=1.50 min; MS (ESIpos): m/z=372 [M+H]$^+$.

Example 41

2-(5-Oxo-4-pyridin-3-yl-2,5-dihydro-1H-pyrazol-1-yl)-isonicotinic acid

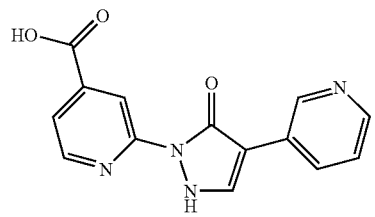

200 mg (760 μmol) of the compound from Example 29 are suspended in a mixture of 6 ml ethanol and 4 ml water, 0.6 ml 50% strength sodium hydroxide solution are added and the mixture is heated under reflux for 1 h. After cooling, a weakly acid pH is established with 1 M hydrochloric acid and the precipitate is filtered off with suction, washed with water and dried.

Yield: 180 mg (84% of th.)

$^1$H-NMR (400 MHz, DMSO-d$_6$): δ=9.11 (d, 1H), 8.86 (s, 1H), 8.62 (d, 1H), 8.46 (s, 1H), 8.32 (dd, 1H), 8.28 (dt, 1H), 7.69 (dd, 1H), 7.36 (dd, 1H).

LC-MS (Method 1): R$_t$=2.19 min; MS (ESIpos): m/z=283 [M+H]$^+$.

Example 42

2-(5-Oxo-4-pyridin-3-yl-2,5-dihydro-1H-pyrazol-1-yl)-isonicotinic acid methyl ester

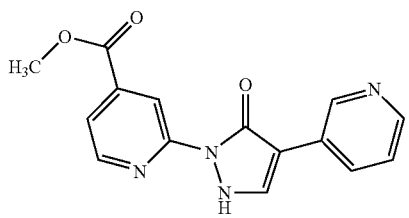

150 mg (531 μmol) of the compound from Example 41 are dissolved in 20 ml methanol, 1 ml concentrated sulfuric acid are added and the mixture is heated under reflux overnight. After cooling, the precipitate formed is filtered off with suction, washed with methanol and dried.

Yield: 117 mg (74% of th.)

$^1$H-NMR (400 MHz, DMSO-d$_6$): δ=9.41 (d, 1H), 8.99-8.94 (m, 2H), 8.86 (s, 1H), 8.71 (d, 1H), 8.66 (d, 1H), 8.01 (dd, 1H), 7.78 (dd, 1H), 3.96 (s, 3H).

LC-MS (Method 4): $R_t$=1.03 min; MS (ESIpos): m/z=297 [M+H]$^+$.

Example 43

2-[4-(Hydroxymethyl)pyridin-2-yl]-4-pyridin-3-yl-1,2-dihydro-3H-pyrazol-3-one hydrochloride

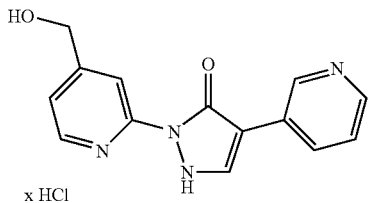

197 mg (1.77 mmol) calcium chloride and 319 mg (8.44 mmol) sodium borohydride are initially introduced into 26 ml ethanol, 50 mg (169 μmol) of the compound from Example 42 are added in portions at 0° C. and the mixture is stirred overnight at RT. The reaction mixture is adjusted to a slightly acid pH by addition of 1 M hydrochloric acid and concentrated and the residue is purified by means of preparative HPLC(RP18 column; mobile phase: acetonitrile/water gradient with addition of 0.1% conc. hydrochloric acid).

Yield: 32 mg (63% of th.)

$^1$H-NMR (400 MHz, DMSO-d$_6$): δ=9.34 (s, 1H), 8.93 (d, 1H), 8.66 (s, 1H), 8.58 (d, 1H), 8.42 (d, 1H), 8.36 (s, 1H), 8.00 (dd, 1H), 7.34 (d, 1H), 4.68 (s, 2H).

LC-MS (Method 1): $R_t$=2.14 min; MS (ESIpos): m/z=269 [M+H]$^+$.

Example 44

5-(3-Oxo-2-pyridin-2-yl-2,3-dihydro-1H-pyrazol-4-yl)-nicotinic acid

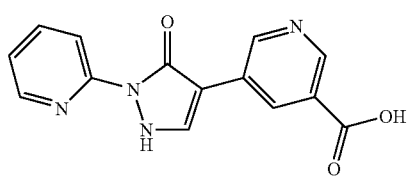

100 mg (380 μmol) of the compound from Example 14 are suspended in a mixture of 3 ml ethanol and 2 ml water, 0.3 ml 50% strength sodium hydroxide solution are added and the mixture is heated under reflux for 2 h. After cooling, the precipitate is filtered off with suction, washed with diethyl ether and dried.

Yield: 50 mg (47% of th.)

$^1$H-NMR (400 MHz, DMSO-d$_6$): δ=9.04 (d, 1H), 8.47-8.42 (m, 2H), 8.36-8.33 (m, 2H), 7.75-7.70 (m, 1H), 7.68 (s, 1H), 7.01-6.97 (m, 1H). LC-MS (Method 5): $R_t$=1.28 min; MS (ESIpos): m/z=283 [M+H]$^+$.

Example 45

N-Methyl-5-(3-oxo-2-pyridin-2-yl-2,3-dihydro-1H-pyrazol-4-yl)-nicotinamide

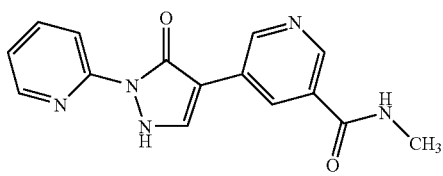

45.0 mg (159 μmol) of the compound from Example 44 are dissolved in 1 ml DMF, 1.9 mg (16 μmol) 4-N,N-dimethylaminopyridine, 24.7 mg (191 μmol) N,N-diisopropylethylamine and 100 mg (191 μmol) (benzotriazol-1-yloxy)-tripyrrolidinophosphonium hexafluorophosphate are added and the mixture is stirred at RT for 15 min. 120 μl (239 μmol) of a 2 M solution of methylamine in THF are added and the mixture is stirred overnight at RT. To bring the conversion to completion, a further 120 μl (239 μmol) of the 2 M solution of methylamine in THF are added and the mixture is stirred again overnight at RT. The reaction mixture is purified directly by means of preparative HPLC (RP18 column; mobile phase: acetonitrile/water gradient).

Yield: 23 mg (49% of th.)

$^1$H-NMR (400 MHz, DMSO-d$_6$): δ=9.18 (s, 1H), 8.74 (d, 1H), 8.64-8.57 (m, 2H), 8.53-8.44 (m, 2H), 8.40-8.25 (m, 1H), 8.09-8.03 (m, 1H), 7.40-7.34 (m, 1H), 2.83 (d, 3H).

LC-MS (Method 3): $R_t$=1.21 min; MS (ESIpos): m/z=296 [M+H]$^+$.

Example 46

N-{[2-(5-Oxo-4-pyridin-3-yl-2,5-dihydro-1H-pyrazol-1-yl)pyridin-4-yl]methyl}-2-phenylacetamide hydrochloride

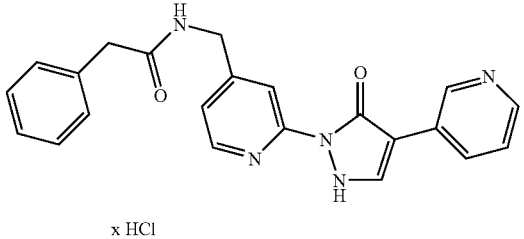

80.0 mg (235 μmol) of the compound from Example 35 and 35.2 mg (259 μmol) phenylacetic acid are dissolved in 5 ml DMF, 119 mg (1.18 mmol) triethylamine, 90.2 mg (470 μmol) 1-(3-dimethylaminopropyl)-3-ethylcarbodiimide hydrochloride and 127 mg (941 μmol) 1-hydroxy-1H-benzotriazole hydrate are added, while cooling with ice, and the mixture is stirred overnight at RT. The precipitate is filtered off and the filtrate is purified by means of preparative HPLC (RP18 column; mobile phase: acetonitrile/water gradient with addition of 0.1% conc. hydrochloric acid).

Yield: 58 mg (57% of th.)

¹H-NMR (400 MHz, DMSO-d₆): δ=9.38 (d, 1H), 8.97 (dt, 1H), 8.88 (t, 1H), 8.72 (s, 1H), 8.62 (d, 1H), 8.41 (d, 1H), 8.29 (s, 1H), 8.04 (dd, 1H), 7.36-7.29 (m, 4H), 7.26-7.21 (m, 2H), 4.42 (d, 2H), 3.56 (s, 2H).

LC-MS (Method 3): $R_t$=1.30 min; MS (ESIpos): m/z=386 [M+H]⁺.

Example 47

N-{[2-(5-Oxo-4-pyridin-3-yl-2,5-dihydro-1H-pyrazol-1-yl)pyridin-4-yl]methyl}acetamide hydrochloride

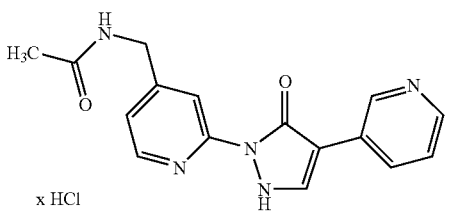

80.0 mg (235 µmol) of the compound from Example 35 are dissolved in 5 ml DMF, 71.4 mg (705 µmol) triethylamine and 20.3 mg (259 µmol) acetyl chloride are added, while cooling with ice, and the mixture is stirred overnight at RT. The reaction mixture is purified directly by means of preparative HPLC (RP18 column; mobile phase: acetonitrile/water gradient with addition of 0.1% conc. hydrochloric acid).

Yield: 33 mg (41% of th.)

¹H-NMR (400 MHz, DMSO-d₆): δ=9.37 (s, 1H), 8.97 (d, 1H), 8.71 (s, 1H), 8.68 (t, 1H), 8.61 (d, 1H), 8.43 (d, 1H), 8.26 (s, 1H), 8.03 (dd, 1H), 7.28 (d, 1H), 4.40 (d, 2H), 1.95 (s, 3H).

LC-MS (Method 1): $R_t$=2.09 min; MS (ESIpos): m/z=310 [M+H]⁺.

Example 48

N-{[2-(5-Oxo-4-pyridin-3-yl-2,5-dihydro-1H-pyrazol-1-yl)pyridin-4-yl]methyl}benzamide hydrochloride

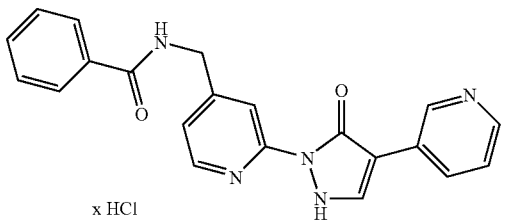

60.0 mg (176 µmol) of the compound from Example 35 are dissolved in 4 ml DMF, 53.5 mg (529 µmol) triethylamine and 27.3 mg (194 µmol) benzoyl chloride are added, while cooling with ice, and the mixture is stirred overnight at RT. The reaction mixture is purified directly by means of preparative HPLC (RP18 column; mobile phase: acetonitrile/water gradient with addition of 0.1% conc. hydrochloric acid).

Yield: 36 mg (50% of th.)

¹H-NMR (400 MHz, DMSO-d₆): δ=9.35-9.29 (m, 2H), 8.91 (d, 1H), 8.68 (s, 1H), 8.59 (d, 1H), 8.44 (d, 1H), 8.34 (s, 1H), 8.01-7.92 (m, 3H), 7.62-7.48 (m, 3H), 7.35 (d, 1H), 4.62 (d, 2H).

LC-MS (Method 4): $R_t$=1.07 min; MS (ESIpos): m/z=372 [M+H]⁺.

Example 49

N-Benzyl-2-(5-oxo-4-pyridin-3-yl-2,5-dihydro-1H-pyrazol-1-yl)-isonicotinamide

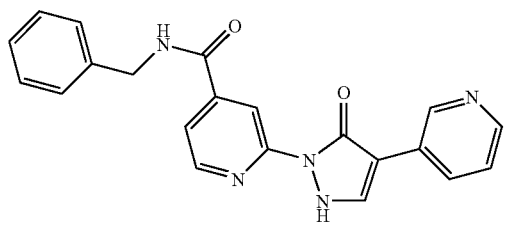

60.0 mg (213 µmol) of the compound from Example 41 are dissolved in 24 ml DMF, 2.6 mg (21 µmol) 4-N,N-dimethylaminopyridine, 65.9 mg (510 µmol) N,N-diisopropylethylamine and 265 mg (510 µmol) (benzotriazol-1-yloxy)-tripyrrolidinophosphonium hexafluorophosphate are added and the mixture is stirred at RT for 45 min. 68.3 mg (638 µmol) benzylamine are added and the mixture is stirred overnight at RT. To bring the conversion to completion, a further 65.9 mg (510 µmol) N,N-diisopropylethylamine and 265 mg (510 µmol) (benzotriazol-1-yloxy)-tripyrrolidinophosphonium hexafluorophosphate are added, the mixture is stirred at RT for 45 min, a further 68.3 mg (638 µmol) benzylamine are added and the mixture is then stirred overnight at RT. It is concentrated and the residue is purified by means of preparative HPLC (RP18 column; mobile phase: acetonitrile/water gradient with addition of 0.1% formic acid).

Yield: 35 mg (44% of th.)

¹H-NMR (400 MHz, DMSO-d₆): δ=9.49 (t, 1H), 9.26 (s, 1H), 8.79 (s, 1H), 8.70-8.62 (m, 3H), 8.52 (d, 1H), 7.76-7.70 (m, 2H), 7.37-7.34 (m, 4H), 7.31-7.24 (m, 1H), 4.52 (d, 2H).

LC-MS (Method 5): $R_t$=1.57 min; MS (ESIpos): m/z=372 [M+H]⁺.

Example 50

3-(4-Chloro-1H-pyrazol-1-yl)-N-{[2-(5-oxo-4-pyridin-3-yl-2,5-dihydro-1H-pyrazol-1-yl)pyridin-4-yl]methyl}propanamide

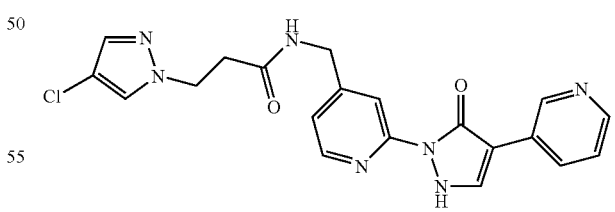

17.5 mg (100 µmol) 3-(4-chloro-1H-pyrazol-1-yl)propanoic acid, 41.7 mg (130 µmol) O-(benzotriazol-1'-yl)-N,N,N',N'-tetramethyluronium tetrafluoroborate and 20.2 mg (200 µmol) triethylamine are dissolved in 0.2 ml DMSO. A solution of 33.9 mg (100 µmol) of the compound from Example 35 in 0.2 ml DMSO is added and the reaction mixture is stirred overnight at RT. The precipitate formed is filtered off and the filtrate is purified by means of HPLC (Method 8).

Yield: 5.8 mg (14% of th.)
LC-MS (Method 8): $R_t$=1.20 min; MS (ESIpos): m/z=424 [M+H]⁺.

The compounds listed in Table 9 are prepared analogously to Example 50 from Example 35 and the corresponding carboxylic acids:

TABLE 9

| Example no. | Structure | MS (ESI) [M + H]⁺; LC-MS $R_t$ [min] (method) | Yield (% of th.) |
|---|---|---|---|
| 51 | 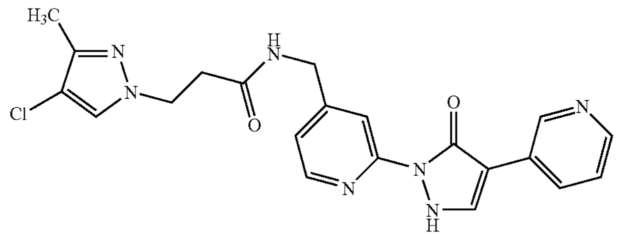 | m/z = 438; 1.27 min (8) | 12 |
| 52 | 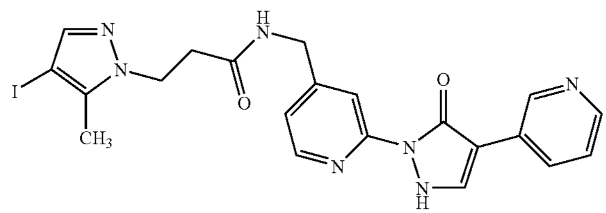 | m/z = 530; 1.32 min (8) | 11 |
| 53 | 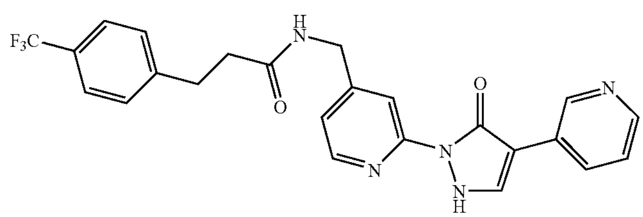 | m/z = 468; 1.48 min (8) | 18 |
| 54 | 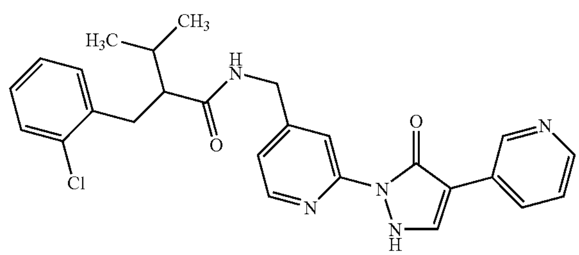 | m/z = 476; 1.60 min (8) | 9 |
| 55 | 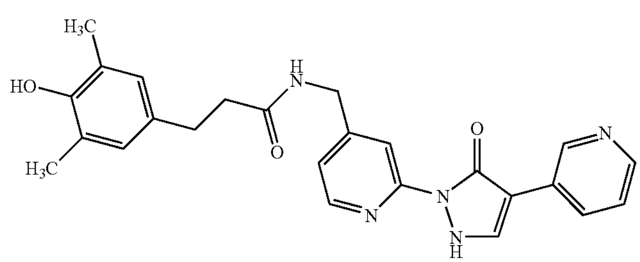 | m/z = 444; 1.28 min (8) | 16 |
| 56 | 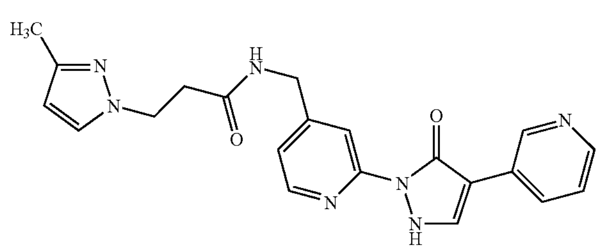 | m/z = 404; 1.13 min (8) | 14 |

TABLE 9-continued

| Example no. | Structure | MS (ESI) [M + H]+; LC-MS R_t [min] (method) | Yield (% of th.) |
|---|---|---|---|
| 57 | 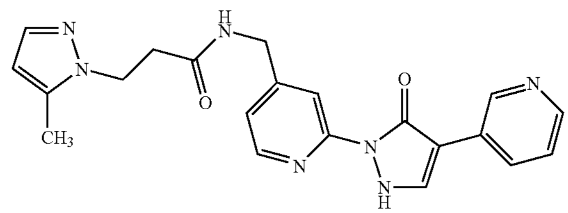 | m/z = 404; 1.11 min (8) | 13 |
| 58 | 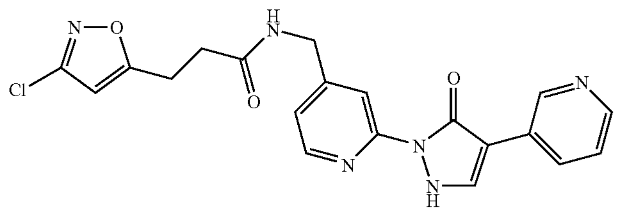 | m/z = 425; 1.21 min (8) | 15 |
| 59 | 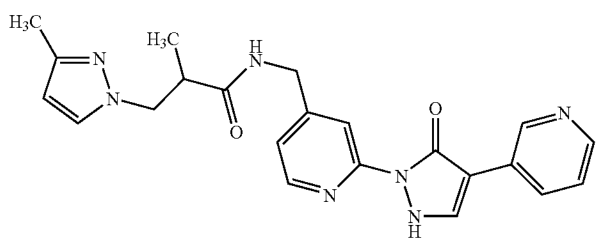 | m/z = 418; 1.16 min (8) | 19 |
| 60 | 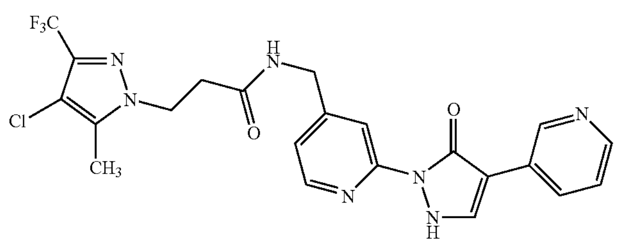 | m/z = 506; 1.48 min (8) | 9 |
| 61 | 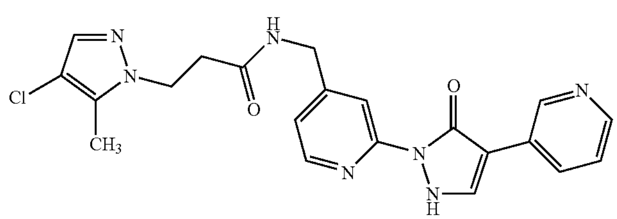 | m/z = 438; 1.27 min (8) | 14 |

[re Example 55: The synthesis of the starting material 3-(4-Hydroxy-3,5-dimethylphenyl)propionic acid is described in *J. Med. Chem.* 1995, 38, 695-707].

B. EVALUATION OF THE PHARMACOLOGICAL ACTIVITY

The pharmacological properties of the compounds according to the invention can be demonstrated in the following assays:
Abbreviations:
DMEM Dulbecco's modified Eagle medium
FCS fetal calf serum
TMB 3,3',5,5'-tetramethylbenzidine
Tris tris(hydroxymethyl)-aminomethane 1. In Vitro Tests for Determination of the Activity and Selectivity of HIF prolyl 4-hydroxylase inhibitors 1.a) Inhibition of the Activity of HIF Prolyl Hydroxylase:

Hydroxylated HIF bonds specifically to the von Hippel-Lindau protein-elongin B-elongin C complex (VBC complex). This interaction occurs only if HIF is hydroxylated on a conserved prolyl radical. It is the basis for the biochemical determination of HIF prolyl hydroxylase activity. The test is carried out as described [Oehme F., Jonghaus W., Narouz-Ott L., Huetter J., Flamme I., Anal. Biochem. 330 (1), 74-80 (2004)]:

A clear 96-well microtiter plate coated with NeutrAvidin HBC (Pierce) is incubated with blocker casein for 30 minutes. The plate is then washed three times with 200 µl each time of wash buffer (50 mM Tris, pH 7.5, 100 mM NaCl, 10% (v/v) blocker casein, 0.05% (v/v) Tween 20) per well. The peptide biotin-DLDLEMLAPYIPMDDDFQL (Eurogentec, 4102 Seraing, Belgium) is added in a concentration of 400 nM in 100 µl wash buffer. This peptide serves as a substrate for the prolyl hydroxylation and is bonded to the microtiter plate. After incubation for 30 minutes, the plate is washed three times with wash buffer, incubated with 1 mM biotin in blocker casein for 30 minutes and then washed again three times with wash buffer.

To carry out the prolyl hydroxylase reaction, the peptide substrate bonded to the plate is incubated with a cell lysate containing prolyl hydroxylase for 1 to 60 minutes. The reaction takes place in 100 µl reaction buffer (20 mM Tris, pH 7.5, 5 mM KCl, 1.5 mM $MgCl_2$, 1 µM-1 mM 2-oxoglutarate, 10 µM $FeSO_4$, 2 mM ascorbate) at room temperature. The reaction mixture moreover contains various concentrations of the prolyl hydroxylase inhibitor to be tested. The test substance is preferably, but not exclusively, employed at concentrations of between 1 nM and 100 µM. The reaction is stopped by washing the plate three times with wash buffer.

For quantitative determination of the prolyl hydroxylation, a fusion protein which contains both thioredoxin from *E. coli* and the VBC complex is added in 80 µl bonding buffer (50 mM Tris, pH 7.5, 120 mM NaCl). After 15 minutes, 10 µl of a solution of polyclonal anti-thioredoxin antibodies from rabbit in bonding buffer are added. After a further 30 minutes, 10 µl of a solution of anti-rabbit immunoglobulin coupled to horseradish peroxidase in bonding buffer are added. After incubation at room temperature for 30 minutes, the plate is washed three times with wash buffer in order to remove non-bonded VBC complex and antibodies. To determine the amount of bonded VBC complex, the plate is incubated with TMB for 15 minutes. The color reaction is ended by addition of 100 µl 1 M sulfuric acid. The amount of bonded VBC complex is determined by measurement of the optical density at 450 nm. It is proportional to the amount of hydroxylated proline in the peptide substrate.

Alternatively, a VBC complex coupled to europium (Perkin Elmer) can be used for detection of the prolyl hydroxylation. In this case, the amount of bonded VBC complex is determined by the fluorescence with respect to time. The use of VBC complex labeled with [$^{35}$S]-methionine is moreover possible. For this, the radioactively labeled VBC complex can be prepared by in vitro transcription-translation in reticulocyte lysate.

The compounds according to the invention inhibit the activity of HIF prolyl hydroxylase in this test with an $IC_{50}$ value of ≦10 µM. Representative results are shown in Table 10:

TABLE 10

| Example no. | $IC_{50}$ [µM] |
|---|---|
| 6 | 0.43 |
| 23 | 0.86 |
| 26 | 0.76 |
| 34 | 0.18 |
| 35 | 2.3 |
| 43 | 1.5 |
| 46 | 0.70 |
| 47 | 2.2 |

TABLE 10-continued

| Example no. | $IC_{50}$ [µM] |
|---|---|
| 48 | 1.9 |
| 50 | 1.9 |

1.b) Cellular, Functional In Vitro Test:

The activity of the compounds according to the invention is quantified with the aid of a recombinant cell line. The cell is originally derived from a human lung carcinoma cell line (A549, ATCC: American Type Culture Collection, Manassas, Va. 20108, USA). The test cell line is transfected in a stable manner with a vector which contains the reporter gene of *Photinus pyralis* luciferase (called luciferase in the following) under the control of an artificial minimal promoter. The minimal promoter comprises two hypoxia-responsible elements upstream of a TATA box [Oehme F., Ellinghaus P., Kolkhof P., Smith T. J., Ramakrishnan S., Hütter J., Schramm M., Flamme I., Biochem. Biophys. Res. Commun. 296 (2), 343-9 (2002)]. Under the effect of hypoxia (e.g. culturing in the presence of 1% oxygen for 24 hours) or under the action of non-selective dioxygenase inhibitors (e.g. desferroxamine in a concentration of 100 µM, cobalt chloride in a concentration of 100 µM or N-oxalylglycine diethyl ester in a concentration of 1 mM), the test cell line produces luciferase, which can be detected and quantified with the aid of suitable bioluminescence reagents (e.g. Steady-Glo® Luciferase Assay System, Promega Corporation, Madison, Wis. 53711, USA) and a suitable luminometer.

Test procedure: On the day before the test, the cells are plated out in an exactly calculated amount of culture medium (DMEM, 10% FCS, 2 mM glutamine) in 384- or 1,536-well microtiter plates and kept in a cell incubator (96% atmospheric humidity, 5% v/v $CO_2$, 37° C.). On the test day, the test substances are added to the culture medium in graduated concentrations. No test substance is added to the cells in batches serving as negative controls. As a positive control for determination of the sensitivity of the cell to inhibitors, desferroxamine e.g. is added in a final concentration of 100 µM. Six to 24 hours after transfer of the test substances into the wells of the microtiter plate, the resulting light signal is measured in the luminometer. A dose/effect relationship is plotted with the aid of the measurement values, which serves as the basis for determining the half-maximum active concentration (call the $EC_{50}$ value in the following).

The compounds according to the invention have $EC_{50}$ values of ≦30 µM in the test described here. Representative results are shown in Table 11:

TABLE 11

| Example no. | $EC_{50}$ [µM] |
|---|---|
| 6 | 4.9 |
| 23 | 13.4 |
| 26 | 6.0 |
| 34 | 4.7 |
| 35 | 17.2 |
| 43 | 7.6 |
| 46 | 7.4 |
| 47 | 12.4 |
| 48 | 18.9 |
| 50 | 7.1 |

1.c) Cellular, Functional In Vitro Test of Modification of the Gene Expression:

To investigate the modification of the expression of specific mRNAs in human cell lines after treatment with test substance, the following cell lines are cultured on 6- or 24-well plates: human hepatoma cells (HUH, JCRB Cell Bank, Japan), human embryonal kidney fibroblasts (HEK/293, ATCC, Manassas, Va. 20108, USA), human cervical carcinoma cells (HeLa, ATCC, Manassas, Va. 20108, USA), human umbilical vein endothelial cells (HUVEC, Cambrex, East Rutherford, N.J. 07073, USA). 24 hours after addition of the test substances, the cells are washed with phosphate-buffered saline and the total RNA is obtained from them using a suitable method (e.g. Trizol® reagent, Invitrogen GmbH, 76131 Karlsruhe, Germany).

For a typical analysis experiment, 1 μg each of the total RNA obtained in this way is digested with DNase I and translated into a complementary DNA (cDNA) using a suitable reverse transcriptase reaction (ImProm-II Reverse Transcription System, Promega Corporation, Madison, Wis. 53711, USA). 2.5% of the cDNA batch obtained in this way is used in each case for the polymerase chain reaction. The expression level of the mRNA of the genes to be investigated is investigated by means of the *real time quantitative polymerase chain reaction* [TaqMan-PCR; Heid C. A., Stevens J., Livak K. J., Williams P. M., Genome Res. 6 (10), 986-94 (1996)] using an ABI Prism 7700 sequence detection instrument (Applied Biosystems, Inc.). The primer-probe combinations used here are generated by means of Primer Express 1.5 Software (Applied Biosystems, Inc.). Specifically, the mRNAs of erythropoietin, carboanhydrase IX, lactate dehydrogenase A and vascular endothelial cell growth factor are investigated.

Substances according to the present invention lead to a significant dose-dependent increase in the mRNA of hypoxia-induced genes in cells of human origin.

2. In Vivo Tests for Detection of the Action in the Cardiovascular System 2.a) In Vivo Test of Modification of Gene Expression:

The test compounds dissolved in suitable solvents are administered to mice or rats either orally by stomach tube administration, intraperitoneally or intravenously. Typical dosages are 0.1, 0.5, 1, 5, 10, 20, 50, 100 and 300 mg substance per kg of body weight and administration. Control animals receive only solvent. 4, 8 or 24 hours after administration of the test substance the animals are sacrificed with an overdoes of isoflurane and a subsequent fracture of the neck and the organs to be investigated are removed. Parts of the organs are shock-frozen in liquid nitrogen. Total RNA is obtained from the organ parts as described under B.1.a) and this is translated into a cDNA. The expression level of the mRNA of the genes to be investigated is investigated by means of the *real time quantitative polymerase chain reaction* [TaqMan-PCR; Heid-C.A., Stevens J., Livak K. J., Williams P. M., Genome Res. 6 (10), 986-94 (1996)] using an ABI Prism 7700 sequence detection instrument (Applied Biosystems, Inc.).

Substances according to the present invention lead to a significant dose-dependent increase in the mRNA of erythropoietin in the kidney after oral or parenteral administration compared with the placebo control.

2.b) Determination of the Erythropoietin Level in Serum:

The test substance in a suitable solvent is administered to mice or rats either intraperitoneally or orally once or twice daily. Typical dosages are 0.1, 0.5, 1, 5, 10, 20, 50, 100 and 300 mg substance per kg of body weight and administration. Placebo control animals receive only solvent. Before the administration and four hours after the last administration of substance, 50 μl of blood are taken from the animals from the retroorbital venous plexus or the tail vein under short narcosis. The blood is rendered uncoagulable by addition of lithium heparin. The blood plasma is obtained by centrifugation. The content of erythropoietin in the blood plasma is determined with the aid of an erythropoietin-ELISA (Quantikine® mouse Epo Immunoassay, R&D Systems, Inc., Minneapolis, USA) in accordance with the manufacturer's instructions. The measurement values are converted into pg/ml with the aid of a reference measurement recorded for mouse erythropoietin.

Substances according to the present invention lead to a significant dose-dependent increase in the plasma erythropoietin after oral and parental administration compared with the starting value and the placebo control.

2.c) Determination of the Cell Composition of Peripheral Blood:

The test substance in a suitable solvent is administered to mice or rats either intraperitoneally or orally once or twice daily for several days. Typical dosages are e.g. 0.1, 0.5, 1, 5, 10, 20, 50, 100 and 300 mg substance per kg of body weight and administration. Control animals receive only solvent. At the end of the study, blood is taken from the animals from the venous plexus of the corner of the eye or the tail vein under short narcosis and is rendered uncoagulable by addition of sodium citrate. The concentrations of erythrocytes, leukocytes and thrombocytes are determined in the blood samples in a suitable electronic measuring apparatus. The concentration of the reticulocytes is determined by microscope screening of in each case 1,000 erythrocytes with the aid of blood smears stained with a stain solution suitable for this purpose (KABE Labortechnik, Nümbrecht). For determination of the hematocrit, blood is taken from the retroorbital venous plexus by means of a hematocrit capillary and the hematocrit value is read off manually after centrifugation of the capillary in a centrifuge suitable for this purpose.

Substances according to the present invention lead to a significant dose-dependent increase in the hematocrit, the erythrocyte count and the reticulocytes after oral and parenteral administration compared with the starting value and the placebo control.

C. EMBODIMENT EXAMPLES FOR PHARMACEUTICAL COMPOSITIONS

The compounds according to the invention can be converted into pharmaceutical formulations as follows.

Tablet:

Composition:

100 mg of the compound according to the invention, 50 mg lactose (monohydrate), 50 mg maize starch (native), 10 mg polyvinylpyrrolidone (PVP 25) (BASF, Ludwigshafen, Germany) and 2 mg magnesium stearate.

Tablet weight 212 mg. Diameter 8 mm, radius of curvature 12 mm.

Preparation:

The mixture of compound according to the invention, lactose and starch is granulated with a 5% strength solution (w/w) of the PVP in water. After drying, the granules are mixed with the magnesium stearate for 5 minutes. This mixture is pressed with a conventional tablet press (for tablet format see above). A pressing force of 15 kN is used as the recommended value for the pressing.

Suspension for Oral Administration:

Composition:

1,000 mg of the compound according to the invention, 1,000 mg ethanol (96%), 400 mg Rhodigel® (xanthan gum from FMC, Pennsylvania, USA) and 99 g water.

10 ml of oral suspension correspond to an individual dose of 100 mg of the compound according to the invention.

Preparation:

The Rhodigel is suspended in ethanol and the compound according to the invention is added to the suspension. The water is added with stirring. The mixture is stirred for approx. 6 h until swelling of the Rhodigel has ended.

Solution for Oral Administration:

Composition:

500 mg of the compound according to the invention, 2.5 g polysorbate and 97 g polyethylene glycol 400.20 g of oral solution correspond to an individual dose of 100 mg of the compound according to the invention.

Preparation:

The compound according to the invention is suspended in a mixture of polyethylene glycol and polysorbate, while stirring. The stirring operation is continued until solution of the compound according to the invention is complete.

i.v. Solution:

The compound according to the invention is dissolved in a concentration below the saturation solubility in a physiologically acceptable solvent (e.g. isotonic saline solution, glucose solution 5% and/or PEG 400 solution 30%). The solution is subjected to sterile filtration and is transferred into sterile and pyrogen-free injection containers.

The invention claimed is:

1. A compound of the formula (I)

(I)

in which

A represents CH, $R^1$ represents a substituent chosen from the series consisting of $(C_1-C_6)$-alkyl, trifluoromethyl, halogen, cyano, nitro, hydroxyl, $(C_1-C_6)$-alkoxy, amino, $(C_1-C_6)$-alkoxycarbonyl, hydroxycarbonyl and —C(=O)—NH—$R^4$, wherein $(C_1-C_6)$-alkyl in its turn can be substituted by hydroxyl, $(C_1-C_4)$-alkoxy, amino, mono-$(C_1-C_4)$-alkylamino, di-$(C_1-C_4)$-alkylamino or a group of the formula —NH—C(=O)—$R^5$, —NH—C(=O)—NH-$R^6$ or —NH—SO$_2$—$R^7$, wherein $R^5$ denotes $(C_1-C_6)$-alkyl, which can be substituted by hydroxyl, $(C_1-C_4)$-alkoxy or phenyl, or phenyl, wherein phenyl, in turn, can be substituted once to three times in an identical or different manner by halogen, cyano, $(C_1-C_4)$-alkyl, hydroxyl, $(C_1-C_4)$-alkoxy, trifluoromethyl or trifluoromethoxy, $R^6$ denotes $(C_1-C_6)$-alkyl, which can be substituted by hydroxyl or $(C_1-C_4)$-alkoxy, and $R^7$ denotes $(C_1-C_6)$-alkyl, and $R^4$ denotes hydrogen or $(C_1-C_6)$-alkyl, which can be substituted by hydroxyl, $(C_1-C_4)$-alkoxy or phenyl, wherein phenyl in its turn can be substituted by halogen, cyano, $(C_1-C_4)$-alkyl, $(C_1-C_4)$-alkoxy, trifluoromethyl or trifluoromethoxy, $R^2$ represents a substituent chosen from the series consisting of halogen, cyano, nitro, $(C_1-C_6)$-alkyl, trifluoromethyl, hydroxyl, $(C_1-C_6)$-alkoxy, trifluoromethoxy, amino, hydroxycarbonyl and —C(=O)—NH—$R^8$, wherein $(C_1-C_6)$-alkyl and $(C_1-C_6)$-alkoxy in their turn can be substituted by hydroxyl and $R^8$ denotes hydrogen or $(C_1-C_4)$-alkyl, m represents the number 0, 1 or 2, n represents the number 0, 1, 2 or 3, wherein, in the case where $R^1$ or $R^2$ occur several times, their meanings can in each case be identical or different, and $R^3$ represents hydrogen, $(C_1-C_6)$-alkyl or $(C_3-C_7)$-cycloalkyl, or a salt thereof.

2. The compound of claim 1, in which

A represents CH, $R^1$ represents a substituent chosen from the series consisting of $(C_1-C_6)$-alkyl, trifluoromethyl, cyano, nitro, hydroxyl, $(C_1-C_6)$-alkoxy, amino, $(C_1-C_6)$-alkoxycarbonyl and hydroxycarbonyl, $R^2$ represents a substituent chosen from the series consisting of halogen, cyano, nitro, $(C_1-C_6)$-alkyl, trifluoromethyl, hydroxyl, $(C_1-C_6)$-alkoxy, trifluoromethoxy, amino and hydroxycarbonyl, wherein $(C_1-C_6)$-alkyl and $(C_1-C_6)$-alkoxy in their turn can be substituted by hydroxyl, m represents the number 0, 1 or 2, n represents the number 0, 1, 2 or 3, wherein, in the case where $R^1$ or $R^2$ occur several times, their meanings can in each case be identical or different, and $R^3$ represents hydrogen, $(C_1-C_6)$-alkyl or $(C_3-C_7)$-cycloalkyl, or a salt thereof.

3. The compound of the formula (I) as claimed in claim 1, in which

A represents CH, $R^1$ represents a substituent chosen from the series consisting of $(C_1-C_6)$-alkyl, fluorine, chlorine, bromine and —C(=O)—NH—$R^4$, wherein $(C_1-C_6)$-alkyl in its turn can be substituted by hydroxyl, $(C_1-C_4)$-alkoxy, amino, mono-$(C_1-C_4)$-alkylamino, di-$(C_1-C_4)$-alkylamino or a group of the formula —NH—C(=O)—$R^5$, —NH—C(=O)—NH—$R^6$ or —NH—SO—$R^7$, wherein $R^5$ denotes $(C_1-C_6)$-alkyl, which can be substituted by hydroxyl, methoxy, ethoxy or phenyl, or phenyl, wherein phenyl, in turn, can be substituted once to three times in an identical or different manner by fluorine, chlorine, bromine, cyano, methyl, hydroxyl, methoxy, ethoxy, trifluoromethyl or trifluoromethoxy, and $R^6$ and $R^7$ independently of one another denote $(C_1-C_6)$-alkyl, and $R^4$ denotes $(C_1-C_6)$-alkyl, which can be substituted by hydroxyl, methoxy, ethoxy or phenyl, wherein phenyl in its turn can be substituted by fluorine, chlorine, bromine, cyano, methyl, methoxy, ethoxy, trifluoromethyl or trifluoromethoxy, $R^2$ represents a substituent chosen from the series consisting of fluorine, chlorine, bromine, cyano, $(C_1\text{-}C_6)$-alkyl, trifluoromethyl, hydroxycarbonyl and —C(=O)—NH—$R^3$, wherein
  $(C_1\text{-}C_6)$-alkyl in its turn can be substituted by hydroxyl
and
  $R^8$ denotes $(C_1\text{-}C_4)$-alkyl,
m represents the number 0, 1 or 2,
n represents the number 0, 1 or 2,
  wherein, in the case where $R^1$ or $R^2$ occur several times, their meanings can in each case be identical or different,
and
$R^3$ represents hydrogen,
or a salt thereof.

4. The compound of claim 1, in which
A represents CH,
$R^1$ represents a substituent chosen from the series consisting of $(C_1\text{-}C_4)$-alkyl, trifluoromethyl, nitro, $(C_1\text{-}C_4)$-alkoxy, amino and $(C_1\text{-}C_4)$-alkoxycarbonyl,
$R^2$ represents a substituent chosen from the series consisting of chorine, bromine, cyano, $(C_1\text{-}C_4)$-alkyl, trifluoromethyl, hydroxyl, $(C_1\text{-}C_4)$-alkoxy, trifluoromethoxy and amino, wherein $(C_1\text{-}C_4)$-alkyl and $(C_1\text{-}C_4)$-alkoxy in their turn can be substituted by hydroxyl,
m represents the number 0 or 1,
n represents the number 0, 1, 2 or 3,
  wherein, in the case where $R^2$ occurs several times, its meanings can be identical or different,
and
$R^3$ represents hydrogen or methyl,
or a salt thereof.

5. The compound of claim 1, in which
A represents CH,
$R^1$ represents a substituent chosen from the series consisting of $(C_1\text{-}C_4)$-alkyl, fluorine, chlorine, bromine and —C(=O)—NH—$R^4$, wherein
  $(C_1\text{-}C_4)$-alkyl in its turn can be substituted by hydroxyl, amino or a group of the formula —NH—C(=O)—$R^5$ or —NH—C(=O)—NH—$R^6$, wherein
    $R^5$ denotes $(C_1\text{-}C_4)$-alkyl, which can be substituted by phenyl or phenyl,
      wherein phenyl, turn, can in each case be substituted once to three times in an identical or different manner by fluorine, chlorine, methyl or trifluoromethyl,
    and
    $R^6$ denotes $(C_1\text{-}C_4)$-alkyl,
  and
  $R^4$ denotes $(C_1\text{-}C_4)$-alkyl, which can be substituted by phenyl,
$R^2$ represents a substituent chosen from the series consisting of chlorine, bromine, cyano, $(C_1\text{-}C_4)$-alkyl and trifluoromethyl, wherein $(C_1\text{-}C_4)$-alkyl in its turn can be substituted by hydroxyl,
m represents the number 0, 1 or 2,
n represents the number 0, 1 or 2,
  wherein in the case where $R^1$ or $R^2$ occur several times, their meanings can in each case be identical or different,
and
$R^3$ represents hydrogen,
or a salt thereof.

6. A compound of the formula (I-A)

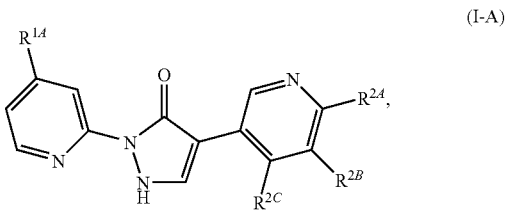

(I-A)

in which
$R_{1A}$ represents hydrogen, methyl or trifluoromethyl
and
$R_{2A}$, $R_{2B}$ and $R^{2C}$ are identical or different and independently of one another represent hydrogen, chlorine, bromine, cyano, methyl, hydroxymethyl, methoxy or ethoxy,
or a salt thereof.

7. A compound of the formula (I-B)

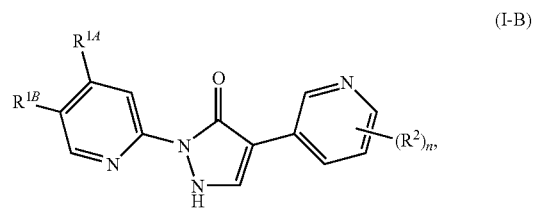

(I-B)

in which
$R^{1A}$ and $R^{1B}$ are identical or different and independently of one another represent hydrogen, fluorine, chlorine, $(C_1\text{-}C_4)$-alkyl or —C(=O)—NH—$R^4$, wherein
  $(C_1\text{-}C_4)$-alkyl in its turn can be substituted by hydroxyl, amino or a group of the formula —NH—C(=O)—$R^5$, wherein
    $R^5$ denotes $(C_1\text{-}C_4)$-alkyl, which can be substituted by phenyl or phenyl,
      wherein phenyl, in turn, can be substituted once to three times in an identical or different manner by fluorine, chlorine, methyl or trifluoromethyl,
  and
  $R^4$ denotes $(C_1\text{-}C_4)$-alkyl, which can be substituted by phenyl,
$R^2$ represents a substituent chosen from the series consisting of chlorine, bromine, cyano, methyl, hydroxymethyl or trifluoromethyl
and
n represents the number 0, 1 or 2,
  wherein, in the case where $R^2$ occurs several times, its meanings can be identical or different,
or a salt thereof.

8. A process for the preparation of a compound of the formula (I), as defined in claim 1, comprising:
reacting a compound of the formula (II)

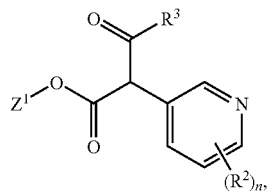

in which $R^2$, $R^3$ and n in each case have the meanings given in claim 1 and
$Z^1$ represents methyl or ethyl,
in an inert solvent, optionally in the presence of an acid, with a compound of the formula (III)

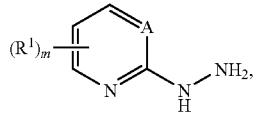

in which A, $R^1$ and m in each case have the meanings given in claim 1,
to give compounds of the formula (IV)

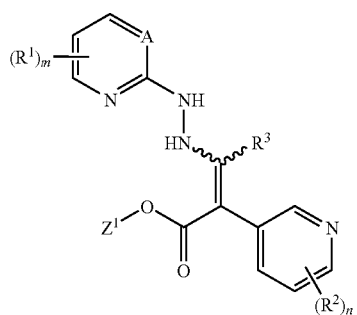

in which $Z^1$, A, $R^1$, $R^2$, $R^3$, m and n have the abovementioned meanings,
cyclizing a compound of formula (IV) in an inert solvent in the presence of a base, thereby producing a compound of the formula (I), (I-A) or (I-B),
and optionally converting the compounds of formula (I), (I-A) or (I-B) corresponding (i) solvents and/or (ii) base or acid into a salt thereof.

9. A process for the preparation of a compound of the formula (I), as defined in claim 1, in which $R^3$ represents hydrogen, comprising:
subjecting a compounds of the formula (V)

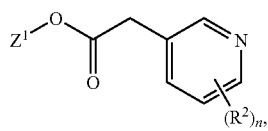

in which $R^2$ and n in each case have the meanings given in claim 1 and
$Z^1$ represents methyl or ethyl,
to a condensation reaction with a compound of the formula (VI)

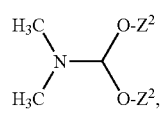

in which
$Z^2$ represents methyl or ethyl,
to give a compounds of the formula (VII)

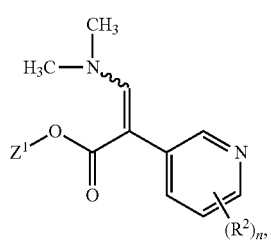

in which $Z^1$, $R^2$ and n have the abovementioned meanings,
reacting the compound of formula (VII) in the presence of an acid with a compound of the formula (III)

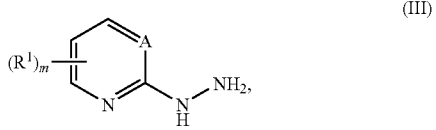

in which A, $R^1$ and m in each case have the meanings given in claim 1, to give compounds of the formula (IV-A)
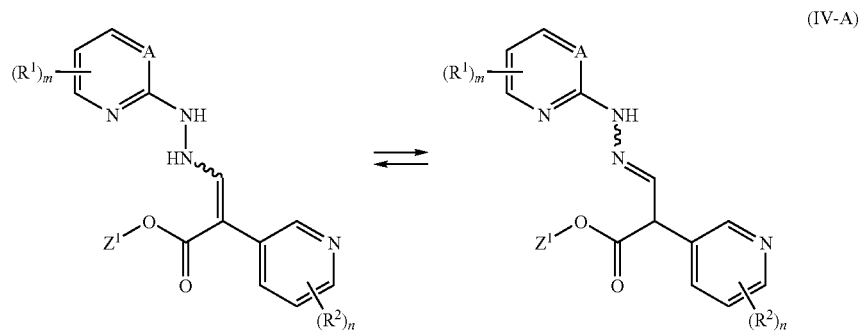
in which $Z^1$, A, $R^1$, $R^2$, m and n have the abovementioned meanings, and cyclizing the compounds of formula (IV-A) in an inert solvent in the presence of a base.
10. A pharmaceutical composition comprising a compound as defined in claim 1 in combination with an inert, non-toxic, pharmaceutically suitable auxiliary substance.
* * * * *